US006780850B1

(12) United States Patent
Dougan et al.

(10) Patent No.: US 6,780,850 B1
(45) Date of Patent: Aug. 24, 2004

(54) EXTENDING THE LIFETIME OF ANTICOAGULANT OLIGODEOXYNUCLEOTIDE APTAMERS IN BLOOD

(75) Inventors: Alfred H. Dougan, Vancouver (CA); Jeffrey I. Weitz, Ancaster (CA)

(73) Assignee: TRIUMF, Vancouver (CA)

( * ) Notice: Subject to any disclaimer, the term of this patent is extended or adjusted under 35 U.S.C. 154(b) by 0 days.

(21) Appl. No.: 09/599,220

(22) Filed: Jun. 22, 2000

Related U.S. Application Data

(60) Provisional application No. 60/139,896, filed on Jun. 22, 1999.

(51) Int. Cl.$^7$ .................... C07H 21/04; A61K 48/00; C12N 15/00
(52) U.S. Cl. .................... 514/44; 536/23.1; 536/24.1; 536/24.5; 435/6; 435/375; 514/2
(58) Field of Search .................... 514/44; 536/23.1, 536/24.1, 24.5; 435/375, 6

(56) References Cited

U.S. PATENT DOCUMENTS 5,688,670 A 11/1997 Szostak et al.
5,756,291 A * 5/1998 Griffin et al. .................. 435/6

FOREIGN PATENT DOCUMENTS

| WO | WO92/14842 A1 | 9/1992 |
| WO | WO92/14843 A1 | 9/1992 |
| WO | WO95/21853 A1 | 8/1995 |
| WO | 9640159 | 12/1996 |
| WO | WO 02/26932 A2 | 4/2002 |

OTHER PUBLICATIONS

Boado, Ruben J. et al, Bioconjugate Chem. 1992, vol. 3, No. 6, pp. 519–523.
Pardridge, William M. et al, Drug Delivery 1, pp. 43–50, 1993.
Tucker, Christopher E. et al, Journal of Chromatography B, 732 (1999) pp. 203–212.
H. Dougan et al., Nuclear Medicine & Biology, vol. 27, 289–297 (2000).
L. C. Bock et al., Nature, vol. 355, 564–566 (Feb. 6, 1992).
H. Dougan et al., Nucleic Acids Research, vol. 25, No. 14, 2897–2901 (1997).
Rosebrough, S.F., "Pharmacokinetics and Biodistribution of Radiolabeled Avidin, Streptavidin and Biotin," Nucl. Med. and Biol. vol. 20, pp. 663–668, 1993.
Pardridge, W.M. et al., "Drug Delivery of Antisense Oligonucleotides or Peptides to Tissues in Vivo Using an Avidin–Biotin System," Drug Delivery 1, pp. 43–50, 1993.
Pardridge W.M. et al., "Enhanced cellular uptake of biotinylated antisense oligonucleotide or peptide mediated by avidin, a cationic protein," FEBS Letters vol. 288, pp. 30–32, 1991.

Kubik, et al. "High–affinity RNA ligands to human α–thrombin" Nucleic Acids Research, 1994, vol. 22, No. 13, pp. 2619–2626.
Latham et al., "The application of a modified nucleotide in aptamer selection: novel thrombin . . . " Nucleic Acids Research, 1994, vol. 22, No. 14, pp. 2817–2822.
Macaya et al., "Structural and Functional Characterization of Potent Antithrombotic Oligonucleotides . . . ", Biochemistry, 1995, vol. 34, No. 13, pp. 4478–4492.
Tasset, et al., "Oligonucleotide Inhibitors of Human Thrombin that Bind Distinct Epitopes", J. Mol. Biol., 1997, vol. 272, pp. 688–698.
Tsiang et al., "Selection of a Suppressor Mutation That Restores Affinity of an Oligonucleotide Inhibitor for Thrombin Using In Vitro Genetics", Journal of Biological Chemistry, vol. 270, No. 33, Aug. 18, 1995, pp. 19370–19376.
"Renal Clearance of Dextran as a Measure of Glomerular Permeability", by Gunnar Wallenius, *ACTA Societatis Medicorum Upsaliensis*, New Series, vol. 59, pp. 1–15 and 84–87.
"Selectivity of Protein Excretion in Patients with the Nephrotic Syndrome", by Gary R. Joachim, et al. *Journal of Clinical Investigation*, vol. 43, No. 12, 1964, pp. 2332–2346.
"Kinetic Characterization of Ribonuclease–Resistant 2'–Modified Hammerhead Ribozymes", by Wolfgang A. Pieken, et al., *Science*, vol. 253, Jul. 19, 1991, pp. 314–317.
"Proteinuria and Aminoaciduria" by Donald E. Oken, *Pathophysiology of the Kidney*, pp. 739–751.
"Pilot Study of the Efficacy of a Thrombin Inhibitor for Use During Cardiopulmonary Bypass" Abe DeAnda, Jr., et al., Thirteenth Annual Meeting of the Society of Thoracic Surgeons, New Orleans, LA, Jan. 31–Feb. 2, 1994, pp. 344–350.
M. Dennis et al., "Albumin Binding as a General Strategy for Improving the Pharmacokinetics of Proteins", J. of Biological Chemistry, vol. 277, No. 38, Sep. 2002, pp. 35035–35043.
M. Savage et al., Avidin–Biotin Chemistry: A Handbook, p. 10.
"Biotin Labelling", Products for DNA Research, Glen Research, p. 20.
B. Chu et al., "Derivatization of unprotected polynucleotides", Nucleic Acids Research, vol. 11, No. 18, 1983.
E. Jablonski et al., "Preparation of oligodeoxynucleotide–alkaline phosphatase conjugates and their use as hybridization probes", Nucleic Acids Research, vol. 14, No. 15, 1986.

(List continued on next page.)

*Primary Examiner*—Sean McGarry
(74) *Attorney, Agent, or Firm*—Birch, Stewart, Solasch & Birch, LLP

(57) ABSTRACT

The present invention is a complex of a polynucleotide having a property of specifically binding to a target protein together with a protein that stabilizes the polynucleotide from degradation and from clearance from the circulation in vivo. Methods for diagnostic imaging and therapeutic uses of the complex are disclosed.

31 Claims, 9 Drawing Sheets

OTHER PUBLICATIONS

Figure 1C:
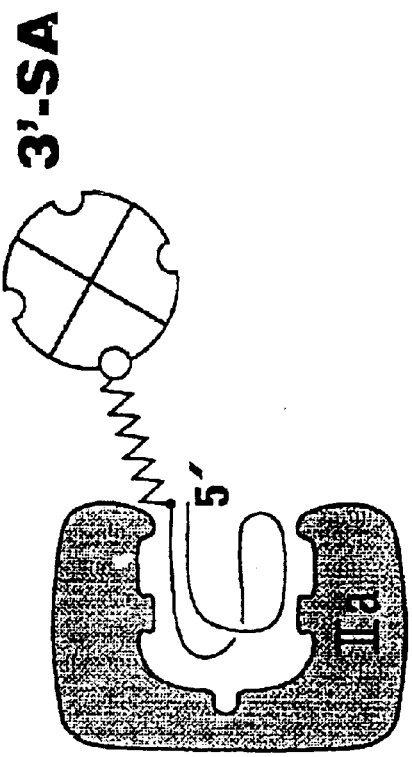

P. Li et al., "Enzyme–linked synthetic oligonucleotide probes: non–radioactive detection of enterotoxigenic *Escherichia coli* in faecal specimens", Nucleic Acids Research, vol. 15, No. 13, 1987.

D. Jellinek et al., "Potent 2'–Amino–2'–deoxypyrimidine RNA Inhibitors of Basic Fibroblast Growth Factor", Biochemistry 1995, vol. 34, pp. 11363–11372.

M. Kubik et al., "Isolation and Characterization of 2'–Fluoro–, '–Amino–, and 2'–Fluoro–/Amino–Modified RNA Ligands to Human IFN–γ That Inhibit Receptor Binding", Journal of Immunology, 1997, 159: 259–267.

D.J. Hnatowich, "Antisense and Nuclear Medicine", J. Nuclear Medicine, vol. 40, No. 4, Apr. 1999, pp. 693–703.

F. Dolle et al., "A General Method for Labeling Oligodeoxynucleotides with $^{18}$F for In Vivo Pet Imaging", J. of Labelled Compounds and Radiopharmaceuticals, vol. 39, No. 4, pp. 319–330.

N. Watanabe et al., "Labeling of Phosphorothioate Antisense Oligonucleotides with Yttrium–90", Nuclear Medicine & Biology, vol. 26, pp. 239–243, 1999.

S. Wagner et al., "Synthesis of Copper–64 and Technetium–99M Labeled Oligonucleotides with Macrocyclic Ligands", Nucleosides & Nucleotides, vol. 16(7–9), pp. 1789–1792, 1997.

TriLink Bio Technologies, Incorporated, "Radioactive Labeling of Oligonucleotides".

S. Osborne, et al., "Aptamers as therapeutic and diagnostic reagents: problems and prospects", Current Opinion in Chemical Biology 1997, 1:5–9.

F. Scheller et al., "New Recognition Elements in Biosensing", Annals of the New York Academy of Sciences, Enzyme Engineering XIV, vol. 864, pp. 37–45, Dec. 1998.

C. Burtis et al. eds., "Tietz Textbook of Clinical Chemistry", c. 1994 by W.B. Saunders, pp. 688–691, 1698–1712, 2114–2118, 2183, 2205, 2208.

C. Burtis et al. eds., Tietz Fundamentals of Clinical Chemistry $4^{th}$ Ed., c. 1996 by W.B. Saunders, pp. 270, 271, 642, 750, 751.

* cited by examiner

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: DNA aptamer directed to thrombin exosite 1

<400> SEQUENCE: 1
ggttggtgtg gttgg                                                      15

<210> SEQ ID NO 2
<211> LENGTH: 29
<212> TYPE: DNA
<213> ORGANISM: Artificial Sequence
<220> FEATURE:
<223> OTHER INFORMATION: DNA aptamer directed to thrombin exosite 2

<400> SEQUENCE: 2
agtccgtggt agggcaggtt ggggtgact                                       29
```

EXTENDING THE LIFETIME OF ANTICOAGULANT OLIGODEOXYNUCLEOTIDE APTAMERS IN BLOOD

RELATED APPLICATIONS

This application claims priority under 35 U.S.C. § 119(e) of U.S. Provisional Application No. 60/139,896, filed Jun. 22, 1999, which is hereby incorporated by reference in its entirety and for all purposes.

FIELD OF THE INVENTION

The present invention relates to compositions comprising polynucleotides that specifically bind to a target protein and to methods for extending the half-life of such polynucleotides in vivo. The compositions are complexes, either covalent or non-covalent, of the polynucleotide and a protein (other than the target protein). The complexes typically include the 5' or 3' end or both of the polynucleotide.

BACKGROUND OF THE INVENTION

Aptamers are nucleic acid sequences that specifically bind to target proteins and other biomolecules (16,30). Aptamers are of interest for imaging, therapy and radiotherapy applications, and they are a unique way to use nucleic acids.

SUMMARY OF THE INVENTION

The present invention is embodied partly in complexes of aptamers with a protein. Complexation of the aptamer with a protein greatly increases the half-life of the aptamer in vivo. The complexes can be non-covalent or covalent. Non-covalent complexes can be formed by covalent attachment of a ligand to the nucleic acid and then complexing the ligand with its specific binding protein.

The aptamer can be one that specifically binds to thrombin. Such aptamers be labeled for detection outside the body and then can be used in methods for imaging blood clots (thrombi) in vivo. In unlabeled form, such aptamers can also be used for inhibiting or preventing coagulation of blood. One problem with such methods is that the half-life of aptamers in serum is typically very short. By complexing the aptamer with a protein (other than the target aptamer binding protein) the half-life of the aptamer in serum is greatly increased. Thus, the present invention provides in vitro methods for imaging thrombi and for inhibiting blood coagulation.

BRIEF DESCRIPTION OP THE DRAWINGS

Figure 1B:
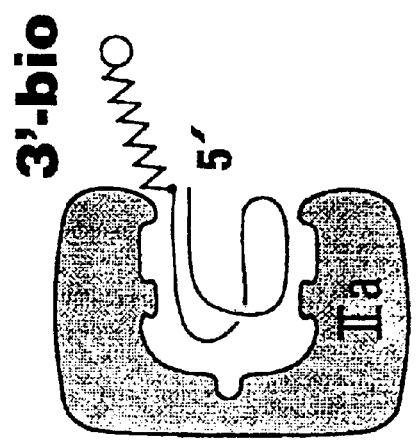
Figure 1A:
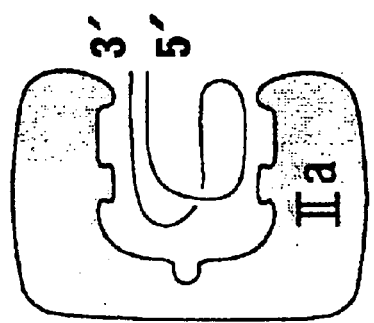

FIG. 1: Schematic representation of complexes between thrombin (IIa) and aptamer (1A), 3'-biotinylated aptamer (1B), and 3'-biotin-streptavidin aptamer (1C). The diagram suggests why modified aptamer nucleotides can diminish affinity, while the 3'-bioconjugate is acceptable.

Figure 2:
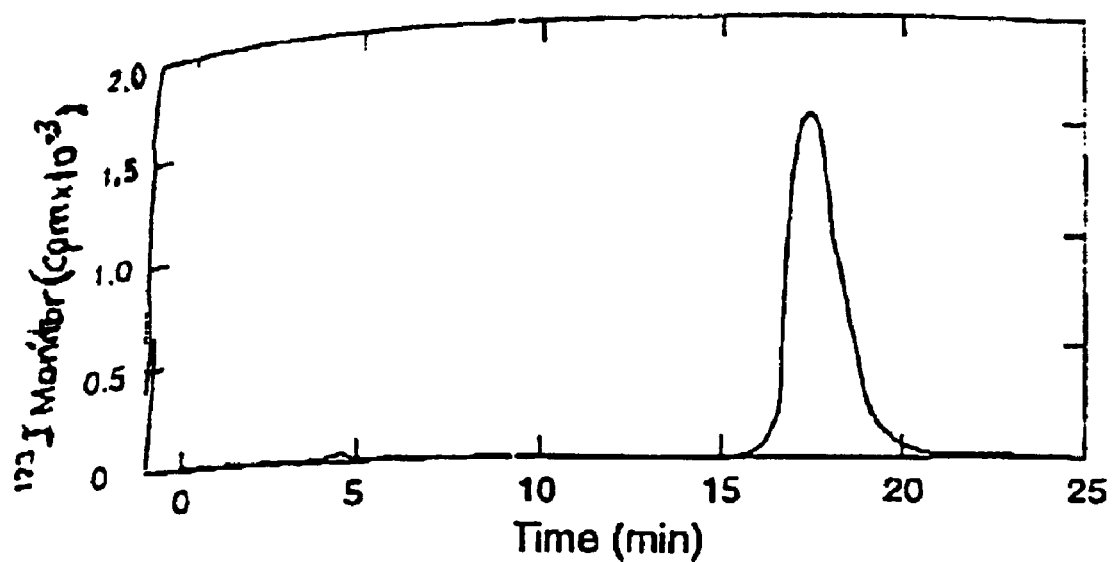

FIG. 2: HPLC radiochromatogram of the product $[^{123}I]$ ODN 2c (180 μCi) following purification of the radioiodinated product through a Sephadex™ G25 column in sodium phosphate (pH 7.0, 0.05M). Reverse phase HPLC employed $CH_3CN$ in TEAB, 1 mL/min.

Figure 3:
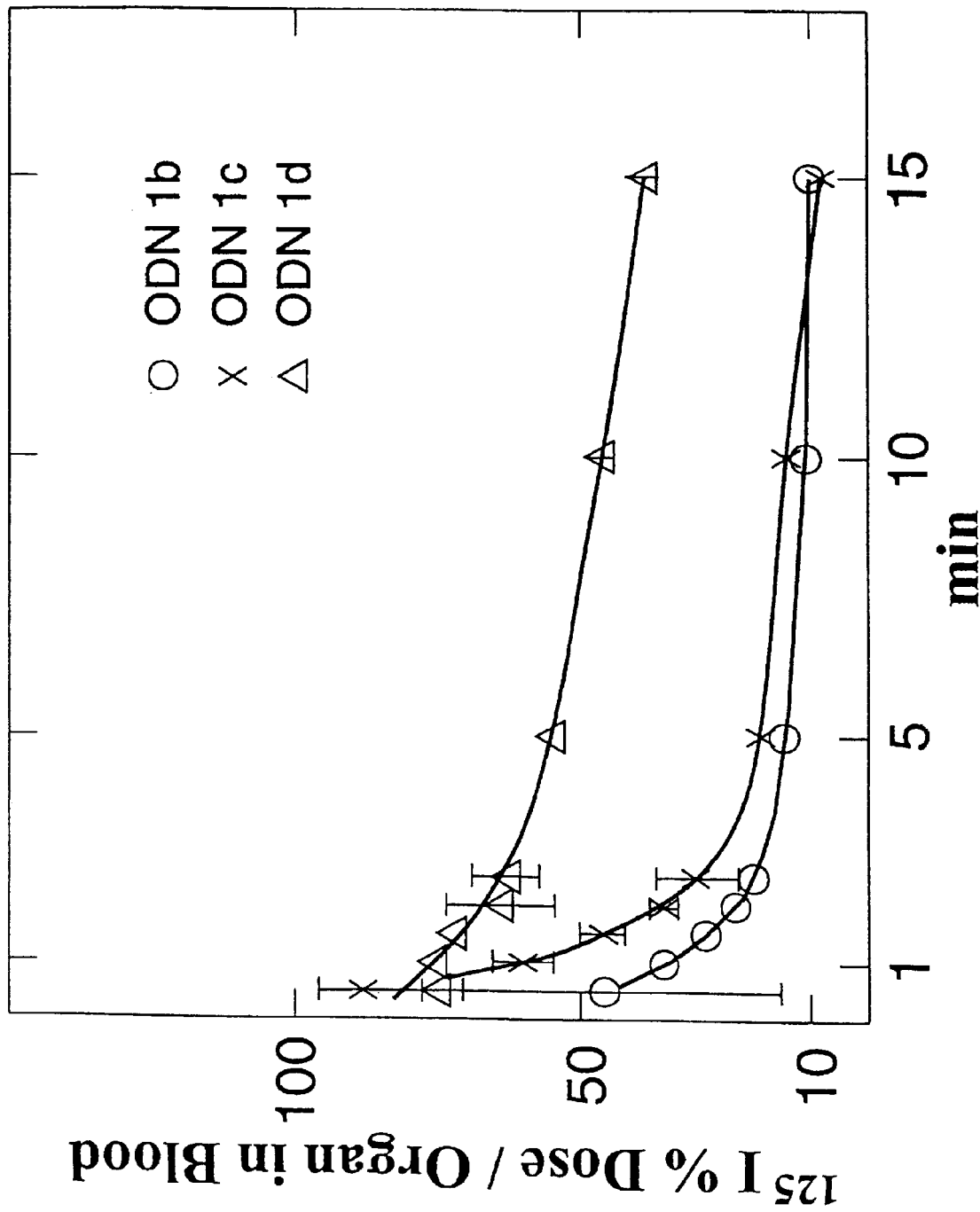

FIG. 3: The $^{125}I$ % dose in total mouse blood is shown following injection of ODN 1b, ODN 1c, and ODN 1d (1 μCi each). Mouse blood was not corrected for DNA content.

Figure 4:
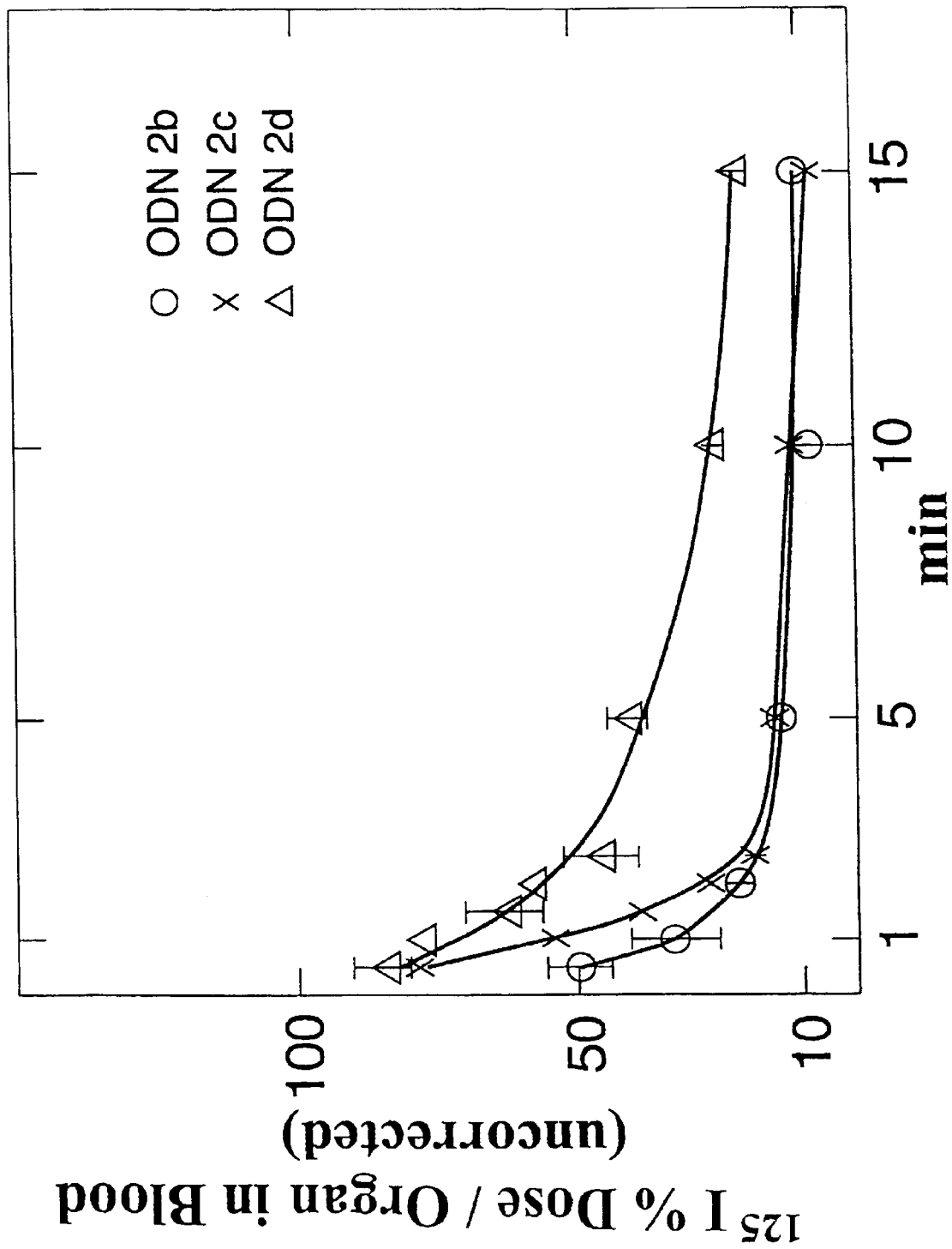

FIG. 4: The $^{125}I$ % dose in total mouse blood is shown following injection of ODN 2b, ODN 2c, and ODN 2d (1 μCi each). Mouse blood was not corrected for DNA content.

Figure 5:
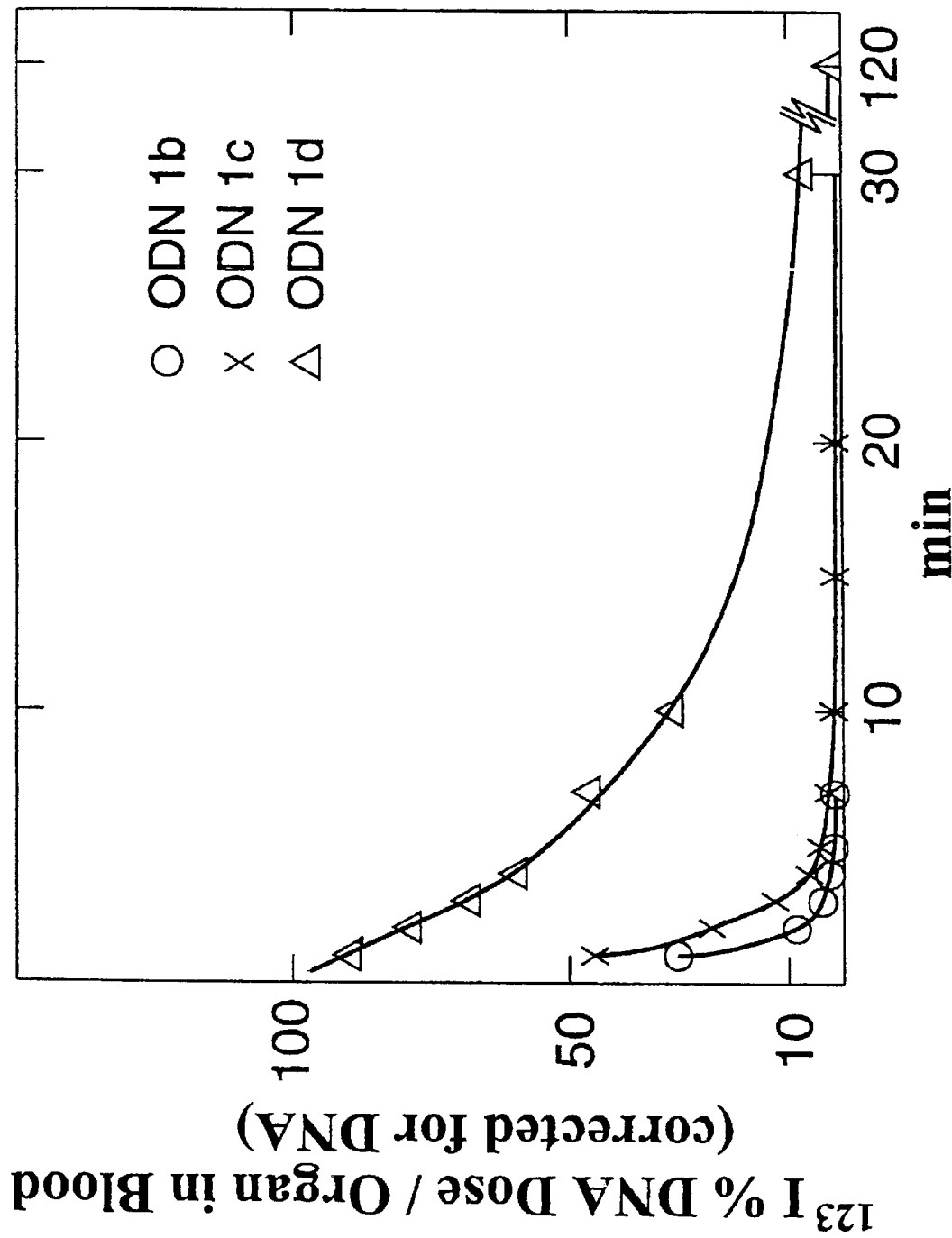

FIG. 5: The $[^{123}I]$DNA % dose in total rabbit blood is shown following injection of 200 μCi ODN 1b, ODN 1c, and ODN 1d (200 μCi each).

Figure 6:
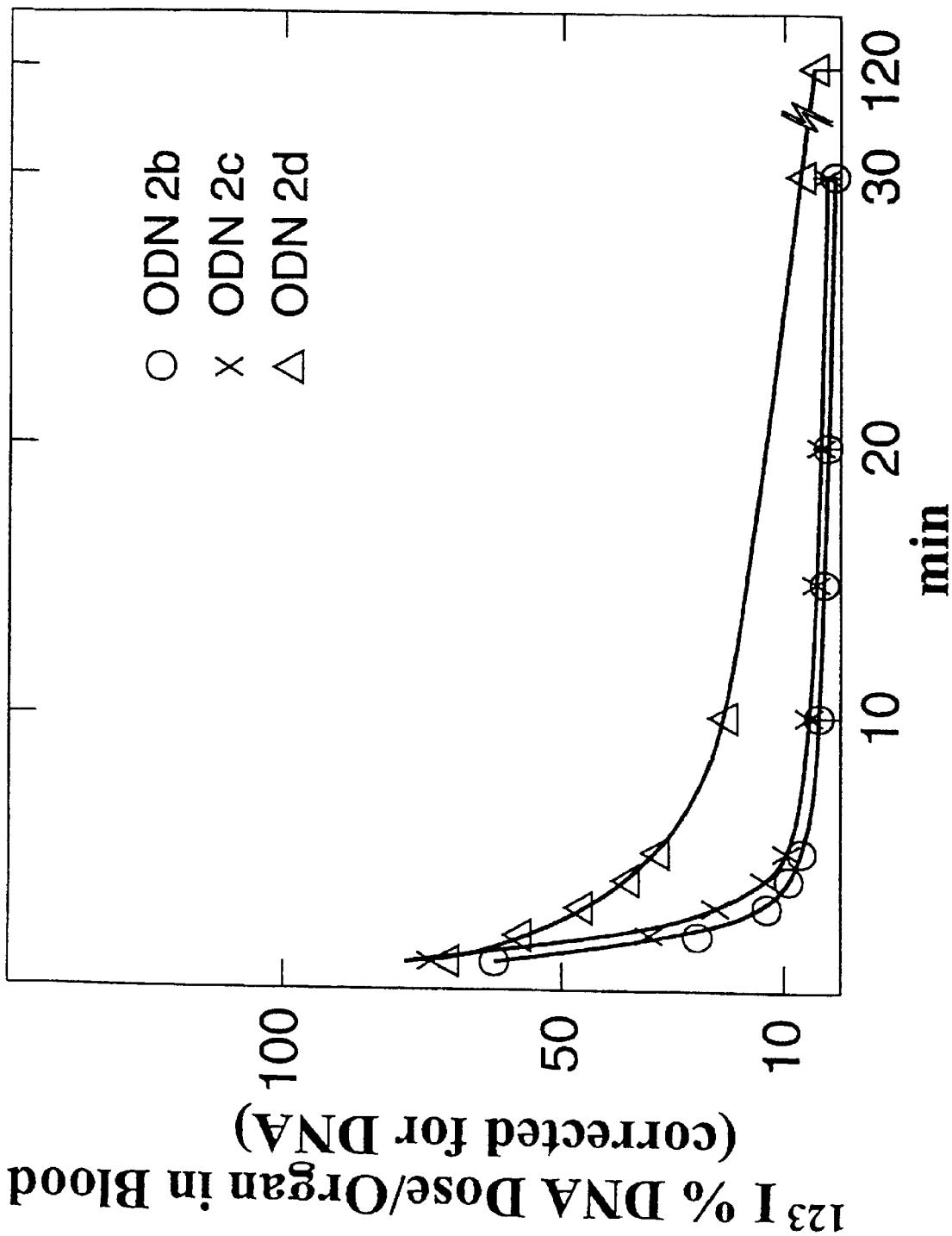

FIG. 6: The $[^{123}I]$DNA % dose in total rabbit blood is shown following injection of 200 μCi ODN 2b, ODN 2c, and ODN 2d (200 μCi each).

Figure 7:
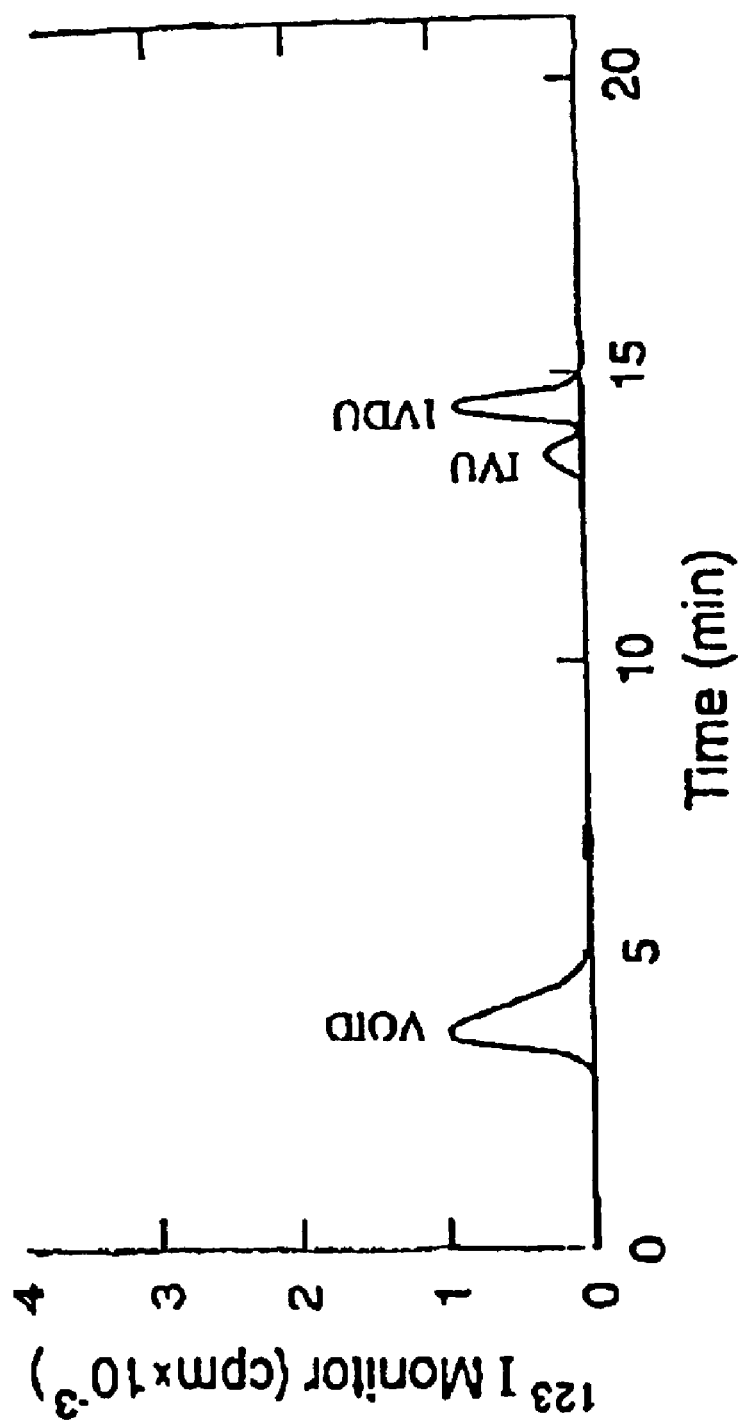

FIG. 7: HPLC radiochromatogram of the metabolites IVDU, IVU, and iodide recovered from rabbit blood 10 min following the injection of $[^{123}I]$ ODN 1b (3.5 mCi). Preparative and HPLC details are given in the legend of Table 5. The tracing of the $^{123}I$ monitor is shown. IVDU and IVU were identified by co-migration with standards.

Figure 8A:
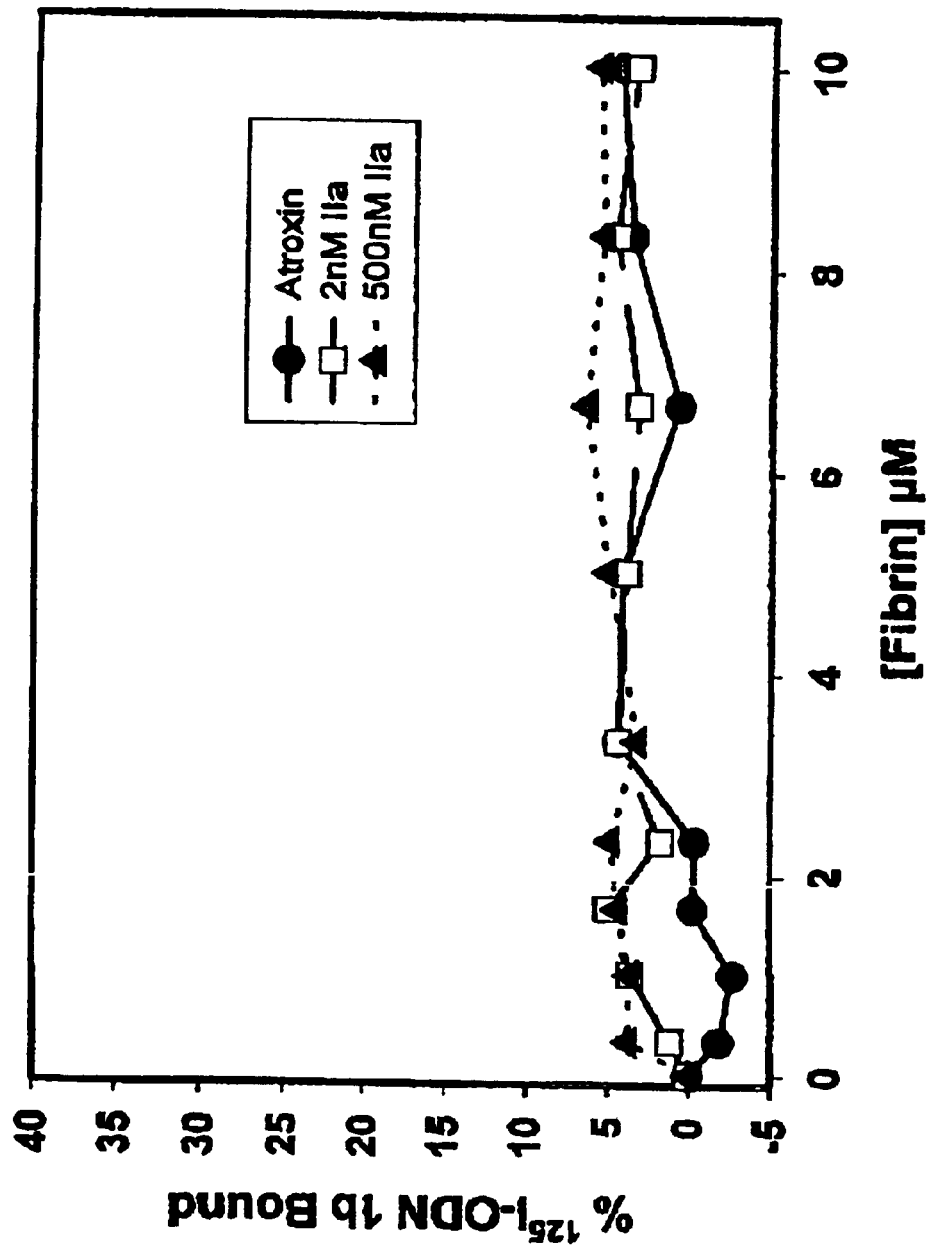
Figure 8B:
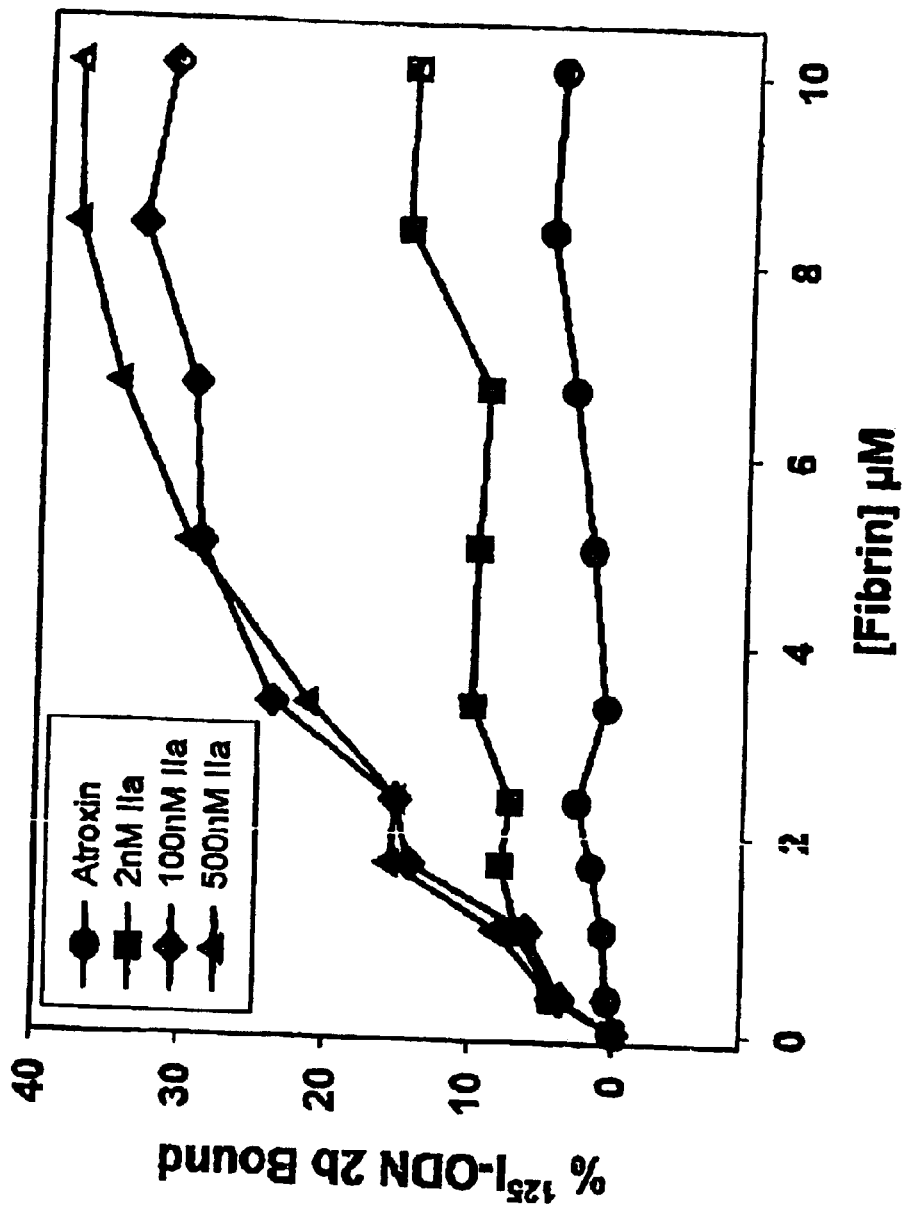

FIG. 8: In situ binding of aptamer to fibrinogen clots. FIG. 8A shows binding of ODN 1b; FIG. 8b shows binding of ODN 2b.

DETAILED DESCRIPTION OF THE INVENTION

Aptamer polynucleotides are typically single-stranded standard phosphodiester DNA (ssDNA). Close DNA analogs can also be incorporated into the aptamer as described below.

A typical aptamer discovery procedure is described below.

1) A polynucleotide comprising a randomized sequence between "arms" having constant sequence is synthesized. The arms can include restriction sites for convenient cloning and can also function as priming sites for PCR primers. The synthesis can easily be performed on commercial instruments.

2) The target protein is treated with the randomized polynucleotide. The target protein can be in solution and then the complexes immobilized and separated from unbound nucleic acids by use of an antibody affinity column. Alternatively, the target protein might be immobilized before treatment with the randomized polynucleotide.

3) The target protein-polynucleotide complexes are separated from the uncomplexed material and then the bound polynucleotides are separated from the target protein. The bound nucleic acid can then be characterized, but is more commonly amplified, e.g. by PCR and the binding, separation and amplification steps are repeated. In many instances, use of conditions increasingly promoting separation of the nucleic acid from the target protein, e.g. higher salt concentration, in the binding buffer used in step 2) in subsequent iterations, results in identification of polynucleotides having increasingly high affinity for the target protein.

4) The nucleic acids showing high affinity for the target proteins are isolated and characterized. This is typically accomplished by cloning the nucleic acids using restriction sites incorporated into the arms, and then sequencing the cloned nucleic acid.

The affinity of aptamers for their target proteins is typically in the nanomolar range, but can be as low as the picomolar range. That is $K_d$ is typically 1 pM to 500 nM, more typically from 1 pM to 100 nM. Apatmers having an affinity of $K_d$ in the range of 1 pM to 10 nM are also useful.

Aptamer polynucleotides can be synthesized on a commercially available nucleic acid synthesizer by methods known in the art. The product can be purified by size selection or chromatographic methods.

Aptamer polynucleotides are typically from 10 to 200 nucleotides long, more typically from 10 to 100 nucleotides long, still more typically from 10 to 50 nucleotides long and yet more typically from 10 to 25 nucleotides long. A preferred range of length is from 25 to 50 nucleotides.

The aptamer sequences can be chosen as a desired sequence, or random or partially random populations of sequences can be made and then selected for specific binding to a desired target protein by assay in vitro. Any of the typical nucleic acid-protein binding assays known in the art can be used, e.g. "Southwestern" blotting using either labeled oligonucleotide or labeled protein as the probe. See also U.S. Pat. No. 5,445,935 for a fluorescence polarization assay of protein-nucleic acid interaction.

A major problem is to utilize aptamers in vivo. In vivo, aptamers share with natural DNA a very short lifetime in blood, estimated to be 1–2 minutes. The short lifetime is sometimes attributed to serum nuclease (10). Serum nuclease results in truncated fragments of aptamer DNA, lacking affinity for the target protein.

Two aptamers have been shown to have thrombin binding properties. Aptamer d(GGTTGGTGTGGTTGG) (SEQ ID NO:1) (ODN 1a) is directed against thrombin exosite 1, the fibrinogen binding site (5). Aptamer d(AGTCCGTGGTAGGGCAGGTTGGGGTGACT)(SEQ ID NO:2) (ODN 2a) is directed against exosite 2, the heparin binding site (29). Both ODN 1b and ODN 2b bind readily to free thrombin. Radioiodination of stannyl oligodeoxyribonucleotides has provided high specific activity [$^{123}$I,$^{125}$I] aptamers for this investigation (14).

In vivo observations with aptamer ODN 1a suggested that aptamer is lost from the blood directly to organ extraction (18,27). The lifetime of ODN 1a in serum or blood appeared longer in vitro than in general circulation. Few degradation products were found in circulating blood. Introduction of a heart lung bypass apparatus into a dog increased the half-life of ODN 1a to roughly 10 minutes (11). The extraction hypothesis predicts that aptamer DNA can remain intact in the blood up until extraction, available for thrombus imaging. Rapid clearance by extraction would leave insufficient time for thrombus to be labeled, while blood nuclease could make any labeling short-lived. The present invention addresses these two obstacles to extend the lifetime of aptamer in blood.

For an aptamer to retain affinity for its target protein, the same nucleotide analogs as used in the selection experiment should be used to synthesize the aptamer for practical use. Use of natural DNA nucleotides is preferred. Introduction of nucleotide analogs that abolish the contacts between the aptamer and the target protein, resulting in decreased affinity, should be avoided. The RNA analogs 2'-fluoropyrimidine RNA and 2'-amino-pyrimidine are frequently used in aptamers. Aptamers can be made using natural phosphodiester RNA, but natural RNA aptamers are much more unstable than DNA aptamers in serum or plasma. Thus use of natural RNA aptamers in vivo is more problematic than use of DNA aptamers. The above RNA analogs provide resistance to serum nucleases (2,22), and are also PCR compatible (19). Use of these analogs provides aptamer sequences that are nuclease resistant (17). Nuclease resistance can be asssayed by in vitro serum or plasma assay.

Since the principal serum nuclease is a 3'-exonuclease, protection can be afforded by 3'-end-caps on single stranded DNA (ssDNA) (1,28). The working examples below demonstrate that such end-capping increases the half-life of aptamers in circulating blood in vivo.

The present invention also addresses the problem of organ extraction of the aptamer. Many proteins are quite stable in circulating blood. Clearance of serum proteins by the kidney is well modeled. The working examples below also show that organ extraction may be impeded using a bioconjugate of the aptamer with a serum protein. The bioconjugate should allow the core aptamer sequence to adopt its native configuration with high affinity towards the target protein, while the protein moiety confers longer lifetime in the blood (FIG. 1).

Streptavidin (SA) is a preferred protein for extending the half-life of an aptamer used for thrombus imaging and anticoagulation (3,25). Streptavidin has a natural half-life of 2.5 hours in the circulation of rats and rabbits. The homolog avidin is rapidly cleared from circulation. Variants of streptavidin, wherein the amino acid sequence is changed by truncations, internal deletions, additions of amino acids to either end or internally or substitution of amino acids, can also be used. A cloned DNA encoding streptavidin and useful for making such modified proteins is disclosed in reference 31. Variant streptavidins are disclosed, for example, in reference 32.

Such SA variants, or any protein utilized to stabilize the aptamer according to the present invention, should preferably exhibit a half-life of at least 1.0 hours in the circulation, preferably about 2.5 hours and preferably longer for therapeutic applications. For imaging uses, the half-life of the stabilizing protein is typically from 1 hour to 3 days, preferably from 1 to 3 hours. The half-life of a protein in circulation can be measured by standard pharmacokinetic methods.

SA can be complexed to the aptamer by derivatizing the polynucleotide at its 5' end, its' 3' end (preferable for use in blood) or both ends, with biotin. Methods for this reaction are known in the art. Other ligand-binding protein pairs can also be used as desired. The use of a ligand and its binding protein for complexing the aptamer provides specificity of the site of the complexation. If desired, the ligand can be introduced at other positions in the aptamer polynucleotide by use of an appropriately derivatized nucleotide during the synthesis of the aptamer. Such methods can also be used to provide covalent attachment sites at any position in the aptamer. The ends of the polynucleotide are the preferred positions for covalent attachment of the aptamer-stabilizing protein moiety.

Appropriate nucleotides for aptamer synthesis and their use, and reagents for covalent linkage of proteins to nucleic acids and their use, are considered known in the art.

The aptamer-protein complex of the invention can be labeled and used as a diagnostic agent in vitro in much the same manner as any specific protein-binding agent, e.g. a monoclonal antibody. Thus, an aptamer-protein complex of the invention can be used to detect and quantitate the amount of its target protein in a sample, e.g. a blood sample, to provide diagnosis of a disease state correlated with the amount of the protein in the sample. For example, aptamers that specifically bind complement 3b (33), human thyroid stimulating hormone (34) and human chorionic gonadotropin (35) can be used to assay levels of these proteins in a sample.

The working examples exemplify use of the complexes for diagnostic imaging. In imaging uses, the complexes are labeled so that they can be detected outside the body. Typical labels are radioisotopes, usually ones with short half-lives. The usual imaging radioisotopes, such as $^{123}$I, $^{124}$I, $^{125}$I, $^{131}$I, $^{99m}$TC, $^{186}$Re, $^{188}$Re, $^{64}$Cu, $^{67}$Cu, $^{212}$Bi, $^{213}$Bi, $^{67}$Ga, $^{90}$Y, $^{111}$In, $^{18}$F, $^{3}$H, $^{14}$C, $^{35}$S or $^{32}$p can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

The aptamer-protein complex of the invention, when the aptamer is one that binds thrombin, can be used as an anticoagulant in vitro or in vivo. Thus, a thrombin binding aptamer complex of the invention can be used in in vitro assays in which inhibition of coagulation is necessary. In vivo, the aptamer-protein complex of the invention can be used as a therapeutic anticoagulant or as an imaging agent. The working examples illustrate use of the complexes of the invention as agents for imaging thrombi in vivo. Reference 11 illustrates the use of an aptamer (not complexed with a protein as in the invention) as a short term anticoagulant during open heart surgery. The complexes of the invention can be used in a similar manner.

For use in circulation, the complexes of the invention are formulated for intravenous administration. The formulation of proteins and nucleic acids and complexes thereof for i.v. use is considered known in the art. The dose of the complex that is administered will of course depend upon the particular utility intended.

In a therapeutic or diagnostic setting, it is considered that the dose administered can be determined by standard methods in the art. For diagnostic imaging purposes, a typical dose would be 1–10, preferably 2–5 mCi of $^{123}$, compound suspended in 1 ml of physiological saline.

The specific activity is preferably from 100 to 20,000 Ci/mmole, preferably 5000–20,000 Ci/mmole of the aptamer nucleic acid.

For therapeutic uses a typical effective dose would be one sustaining to 1 to 10 mg of aptamer nucleic acid and 10 to 100 mg of complexing protein, assuming a blood volume of 9 liters. The complex can be administered as an initial dose, followed by sustaining doses, administered at appropriate times depending on the mean life of the complex in vivo. The complex can be administered at a constant rate, e.g. by an intravenous drip. The dose will of course vary depending upon the exact mean life of the aptamer-protein complex and the $K_d$ of the aptamer-protein complex for the target protein. Higher affinity and longer mean life of the complex can provide for lower doses. It is considered within the skill of the practitioner of pharmaceutical arts to determine the effective dose using these considerations and standard methods.

EXAMPLES

The invention is illustrated by the following examples. The examples merely show selected embodiments of the invention and are not limiting of the invention. The scope of the invention is defined by the claims following.

Example 1

Stabilization of a Thrombin Binding Aptamer In Vivo

Materials and Methods

Oligodeoxynucleotides: ODNs were prepared using standard phosphoramidite chemistry by the Nucleic Acids and Protein Service laboratory at the University of British Columbia, Vancouver B.C. Stannyl ODNs and radioiodinated ODNs were prepared by our published procedure (14) (Table 1). 3'-Biotin ODN was prepared using biotin TEG CPG (Glen Research P/N: 10–1963). [$^{123}$I]NaI and [$^{125}$I]NaI in 0.1N NaOH were obtained from Nordion International. ODNs were prepared with specific activity 1,000–2,000 Ci/mmole (125I) or >10,000 Ci/mmole ($^{123}$I). Radioactive ODNs were prepared as the sodium salts, using commercial size exclusion columns, following the supplier's directions (Centri-Spin-10™, Princeton Separations ($^{125}$I); NAP-5, Pharmacia ($^{123}$I); A radiochromatogram of ($^{123}$I) ODN 2c is given in FIG. 2. Streptavidin bioconjugates of ODNs were obtained by incubating the 3'-biotin ODN in phosphate buffered saline with a fourfold excess of streptavidin (Boehringer-Mannheim) for four hours at ambient temperature. The bioconjugate was purified using a Centricon-30™ filter (Millipore) following the supplier's instructions.

Determination of aptamer affinity for thrombin: Human α-thrombin (Enzyme Research) was derivatized with fluorescein-labeled D-Phe-pro-Ala-CH$_2$Cl PPACK) (Haematologic Technologies) blocking the active site (6). Thrombin solution (20 mM Tris, 150 mM NaCl, pH 7.4) was titrated with aptamer. The fluoresence intensity was monitored using a Luminescence Spectrophotometer (LS50b (Perkin Elmer); 492 nm/522 nm), and fit by non-linear regression analysis to equation 10 of reference (7) to estimate kD. Intrinsic fluorescence was measured using the setting 280 nm/340 nm. Carrier streptavidin led to a background of scattered light with ODNs 1f and 2f, so that duplicate measurements were performed.

Pharmacokinetic analysis and radiobiodistribution: Six ODN compositions were investigated in animal biodistribution (Table 1). Animal procedures were approved by the UBC Committee on Animal Care, which follows the recommendations of the Canadian Council for Animal Care. Mouse: Biodistribution studies were carried out using male CDI/UBC mice (20–25 g). Mice were injected in the tail vein with 37 KBq (1 μCi; 0.7 pmole) of [$^{125}$I] ODN in 0.1 mL potassium phosphate buffer, and were sacrificed at given times post injection. The activity of the blood, liver, kidneys, spleen, stomach, lungs, heart, muscle and brain were determined and the results expressed as % injected dose per organ (Table 3A–3F, organs; FIGS. 3 and 4, blood). Rabbit: White female New Zealand rabbits (~3.5 kg) were used for experiments. Rabbits were anaesthetized by the i.m. injection of Ketamine hydrochloride (42 mg/kg), Acepromazine (1.0 mg/kg), and Xylazine (4.2 mg/kg). Rabbits were injected in the marginal ear vein with 0.5 mCi [$^{123}$I] ODN (100 pmole), and the biodistribution was estimated from scintigraphic scans. Each biodistribution is based on data from a single rabbit (Table 4A–4F). For blood studies (FIGS. 5 and 6) rabbits were heparinized (100 U/kg) and approximately 200 μCi [$^{123}$I] ODN (40 pmole) was injected via ear vein; whole blood samples were taken from an artery of the opposite ear, and dispensed into pre-weighed tubes containing EDTA anticoagulant. Blood volume of the rabbit was taken to be 54 mL/kg, 1.050 g/mL (21,23). Following invasive surgical procedures, rabbits were sacrificed by the intravenous injection of Euthanyl™.

Assay of DNA bound $^{123}$I: Total blood [$^{123}$I]DNA in the rabbit was estimated by multiplying the total blood $^{123}$I (in units % dose per organ in blood) by the fraction DNA (as determined by assay) giving the result as [$^{123}$I]% DNA Dose/Organ in blood. Following centrifugation of blood, plasma (25 μL) was assayed by silica column (Sep Pakμ™, Waters) with elution by methanol/acetone (1/1; 2.5 mL) (15) (FIGS. 5 and 6). The silica Sep Pakμ™ assay was shown to retain nucleoside monophosphate and all ODNs while releasing nucleoside and free iodide. Polyacrylamide gel electrophoresis (PAGE) and silica column chromatography were adopted because trichloroacetic acid (TCA) and ethanol precipitation assays are inefficient with short oligonucleotides (<20-mer) derived from aptamers (20).

Plasma Metabolites (26): A female New Zealand rabbit (2.4 kg) was injected with [$^{123}$I]ODN 1b (3.5 mCi) in the marginal ear vein; plasma was obtained from blood samples (0.5 mL), and treated with an equal volume of ice cold methanol (5 min). The supernatant was evaporated, resuspended in aqueous methanol (20% vol/vol), and filtered (0.45 μm). The sample was analyzed using a C18 column (Waters: 8NVC184μ) with a linear gradient of methanol (27% to 62%, 18 min) in $KH_2PO_4$ (0.01M) (2 mL/min) (12,26). The $^{123}I$ peaks corresponded to standard 5-(2-iodovinyl)-2'-deoxyuridine (IVDU) (Prof. L. I. Wiebe) and standard [$^{125}I$]5-(2-iodovinyl)uracil (IVU), (prepared from BrVU(Sigma) (13)). It was assumed that the void represented free iodide (FIG. 7; Table 5).

Digestion of ODNs by blood nuclease: [$^{125}I$] ODN (0.02 μCi, approximately 10 fmole) was suspended in 40 μL blood freshly drawn from a rabbit or mouse. The blood was incubated at simulated body temperature for a series of times (5, 10, 20, 40, 80, and 160 min). Plasma was obtained by centrifugation. Plasma (2.5 μL) was diluted in formamide (10 μL) or else urea (10 μL; urea (7M), glycerol (10%) and incubated 5 min at 95° C. followed by 5 min at 0° C.) and applied to a polyacrylamide sequencing-type gel (20% polyacrylamide (bisacrylamide/acrylamide(1/19)), urea (8M)) for electrophoresis (PAGE). Autoradiography was performed with Kodak Biomax™ MS film and Biomax™ MS image intensifier (Tables 6 and 7).

Results

3'-biotin and 3'-streptavidin conjugates of the aptamers should retain affinity to thrombin (Scheme 1). The affinity (kD) of bioconjugate aptamers (Table 1) for fluorescein PPA-thrombin was measured by fluorometric titration, using an incident wavelength 492 nm and emission wavelength 522 nm (Table 2). Fluorescence takes place with higher characteristic quantum yield in the complex (aptamer and fluorescein PPA-thrombin) than with the free enzyme. Fluorescence measurements during titration allowed estimation of bound versus unbound thrombin as a function of aptamer molarity, and hence calculation the kD. The Ki for inhibition of coagulation by ODN 1f was verified as roughly 100 nM. The kD of ODN 2f in the hydrolysis of Chromozym-thrombin was 10.2 nM.

3'-streptavidin conjugates alone (not unmodified DNA, or 3'-biotin conjugates) showed extended lifetime in blood in vivo. Biological evaluation was carried out with six aptamer analogs, ODNs 1b,c,d and 2b,c,d, (two bioconjugate series; Table 1). For each analog we estimated the mouse and rabbit biodistributions, with a detailed study of rabbit blood. In vitro blood nuclease assays supplemented the in vivo blood studies.

The first example, [$^{125}I$] aptamer ODN 1b, was prepared from the stannyl precursor. The biodistribution was determined in the mouse. Aliquots of aptamer (1 μCi) were injected by tail vein. Mice were sacrificed and $^{125}I$ was measured in selected organs and tissues. Results for times 0–15 min are listed in Table 3A. The $^{125}I$ increased rapidly in several organs, notably the muscle tissue, the liver and the kidney. The organ bound $^{125}I$ commenced to fall within the observation period. The lungs accumulated little $^{125}I$. The blood $^{125}I$ % dose per organ fell rapidly up to 2.5 min (the "early phase"), and at a noticeably slower rate from 2.5 to 15 min (the "late phase") (FIGS. 3 and 4).

Biodistribution in the rabbit was estimated from scintigraphic images (Table 4A). Following injection of [$^{123}I$] ODN 1b (0.5 mCi) images were analyzed for 30 min or more. The heart, liver and kidneys were prominent. Liver uptake reached a maximum, and then diminished. Kidney uptake rapidly attained a maximum; a delay of 10 min preceded the appearance of 123I in the bladder. We found 30–40% of the injected $^{123}I$ in the bladder at 30–60 min post injection. The lungs accumulated little activity; the thyroids were not visible. The gall bladder did not appear in rabbit images. Two anaesthetized rabbits were injected as usual with ODN 1b (50 μCi). Samples of bile were washed from the gall bladder at 5 min intervals. Less than 0.1% of the injected dose was recovered from the gall bladder during the first 40 minutes.

Rabbit blood was analyzed separately from the image, following injection of [$^{123}I$] ODN 1b (200 μCi). Blood was recovered at 30 sec intervals. We observed the $^{123}I$ activity (% dose per organ) rise initially from 50% at 20 sec to a maximum of 66% at 30–40 sec. The $^{123}I$ % dose per organ then decreased rapidly, approaching 24% at 5 minutes. From ~10 min onward, the $^{123}I$ activity decreased more slowly, reaching 17.8% at 30 min. The pattern of $^{123}I$ elimination again suggested an "early" phase and a "late" phase.

The difference between early phase and late phase blood was examined following the injection of ODN 1b into rabbits. In both phases, $^{123}I$ activity was located in the blood plasma following the injection of ODN. Chromatography of plasma revealed that early phase plasma $^{123}I$ bound to $SiO_2$, suggesting that the $^{123}I$ was incorporated into DNA. Late phase plasma $^{123}I$ bound roughly 3% to the $SiO_2$, suggesting that metabolites below the nucleotide monophosphate level predominated in late phase blood (FIGS. 5 and 6). Total blood [$^{123}I$]DNA was estimated by multiplying the total blood $^{123}I$ (in units % dose per organ in blood) by the fraction DNA (as determined by $SiO_2$ chromatography) giving the result in the following units: [$^{123}I$]% DNA Dose/Organ in blood. In the case of ODN 1b, the metabolites in rabbit plasma were identified and characterized by reverse phase HPLC (FIG. 2; Table 5). The major $^{123}I$ peaks coincided with 5-(2-iodovinyl)-2' deoxyuridine (IVDU), 5-(2-iodovinyl)uracil (IVU), and probably free iodide (i.e. the HPLC void). IVDU was the most abundant metabolite at 5 min, while iodide predominated at later times.

Rapid removal of ODN 1b from blood is evidently a serious problem. We attempted to alleviate this problem with the 3'-biotin (ODN 1c) and 3'-streptavidin bioconjugates (ODN 1d) (FIG. 2). Similar bioconjugates of the exosite 2 aptamer (ODNs 2b,c,d) were evaluated to determine whether the results were sequence-specific. A comparative analysis was extended to ODNs 1c,d and 2b,c,d (Tables 3A–F, and 4A–F):

Blood: Modified aptamers behaved in characteristic ways in the blood (FIGS. 3–6), depending on 3'-modification, and not depending much on the DNA sequence. Total blood radioiodine pharmacokinetics was initially measured in, the mouse and rabbit. Repeated mouse results demonstrated statistical validity (i.e. acceptable standard deviation (SD)). Mouse and rabbit results resembled each other. Blood concentrations were initially high, but fell as radiotracer was removed. We have pointed out the "early phase" and "late phase" phenomenon in the blood. The initial blood radioiodine level (% dose per organ) was significantly higher for 3'-biotin aptamers (ODNs 1c and 2c) than unmodified aptamers. The "late phase" blood % dose per organ of 3'-biotin aptamers superimpose upon the levels for unmodified aptamers. Modified aptamers with 3'-SA showed elevated blood radioiodine initially and also later (compared to unmodified and 3'-biotin).

DNA was assayed directly in rabbit plasma (FIGS. 5 and 6). The pharmacokinetics showed prolonged lifetime of aptamer in blood, although the data suggested multicomponent kinetics. Mean lifetime was calculated by numerical integration. For ODN 1d the mean lifetime was estimated 7.9 minutes based on data from 0 min to 30 min, 15.2 min (data from 0 min to 90 min), and 18.6 min (data from 0 min to 120 min). For ODN 2d the mean lifetime was 8.7 min (data 0 min to 30 min), 23 min (data 0 min to 90 min), and 31 min (data 0 min to 120 min). Further clarification of the nature of the long-lived component would be of interest.

To supplement the blood biodistribution data, we developed a simulated in vivo nuclease degradation assay for [$^{125}$I]ODNs. In preliminary work (data not presented), we found that ODN 1b and ODN 2b were both stable in pre-frozen rabbit plasma up to 160 min at 39° C. We developed a nuclease assay in freshly drawn blood (heparinized) from mice or rabbits. At 20–23° C. no digestion of ODN 1b or ODN 2b was observed during 160 min. At simulated body temperature, considerable digestion was observed. Autoradiographs showed mainly the bands from intact ODNs. Faint ladders of truncated ODNs were observed ahead of intact ODN 1b and ODN 2b. Ladders were previously reported in vivo with ODN 1a monitored by HPLC or laser stimulated fluorescence (18,24,27). Ladders were not observed ODNs 1c,d or 2c,d.

Thus, [$^{125}$I]ODNs were incubated in vitro in freshly drawn mouse blood (36° C.) or rabbit blood (39° C.) (Tables 6 and 7). DNA was recovered from the plasma and examined by denaturing PAGE and autoradiography. The halflife of ODNs 1b and 2b were estimated ~10 min in mouse blood or ~5 min in rabbit blood. The halflife of biotinylated ODN 1c was ~160 min in mouse blood or rabbit blood, while the halflife of 2c was ~80 min in mouse blood and ~40 min in rabbit blood. The halflife of the streptavidin bioconjugates 1d and 2d appeared to be 160 min or greater in either mouse blood or rabbit blood.

Liver: Liver uptake showed the highest % dose per organ with nearly all the ODNs, in both the mouse and the rabbit, although uptake in the kidneys and muscle was comparable. The maximum was achieved quickly, at 1–2 min; maximal uptake of streptavidin analogs was delayed to roughly 5 min in the mouse. Liver activity decreased rapidly from the maximum. Mouse liver uptake seemed not to distinguish the pairs 1b/2b and 1c/2c; however the uptake of 2d exceeded 1d. In the rabbit, uptake of ODN 2b,c,d exceeded the corresponding ODN 1b,c,d. With mouse data we have good quantitative and statistical certainty. Mouse liver maxima showed sequence dependence 1b>1c>1d or 2b=2c<2d. Rabbit data differed slightly from this rule. We did not detect the rabbit gall bladder in images.

Kidneys: Kidney % dose per organ was as high as 15%. Broad maxima for ODNs 1b and 2b were observed at 1.0–1.5 min. Maxima for the bioconjugates were observed at increasingly later times, with the maxima for ODNs 1d and 2d at 5 min, and of lesser magnitude. In the mouse kidney, uptake of ODN 2b,c,d exceeded the analogous ODN 1b,c,d. Rabbit images show that the bladder contained 30–40% of the injected dose following ODN 1b injection. Although the kidney/bladder route assumed significance with time, the rabbit bladder was not observed until 10 min postinjection of 1b,c,d or 2b,c,d. This observation suggests that the kidney uptake may represent nearly the total in the kidney/bladder pathway at early times.

Muscle: Mouse muscle showed a low % dose per gram for all ODNs; the % dose per organ assumed significance (up to 27%). Maxima were attained early by 1b or 2b (1 min), later by 1c or 2c (5 min), and still later by 1d or 2d (10–15 min).

Lungs: Mouse lungs attained the highest % dose per gram of the solid organs following the injection of the streptavidin and biotin bioconjugates. Mouse blood showed even higher % dose per gram than the lung in these instances. Lung activity may indicate physiological uptake, or it may reflect contamination of lung tissue with blood. In rabbits we did not observe lung images following the injection of [$^{123}$I] bioconjugate ODN analogs (i.e. 1b,c,d or 2b,c,d).

Thyroids: Thyroids did not image during 30 min scintigraphic studies with rabbits.

The biodistributions reported here generally agree with the biodistribution of tritiated ODN 1a reported in rats (24). Differences may be attributed to IVDU and bioconjugates in our ODNs contrasted to natural DNA in ref (24), and species differences.

Conclusions

Short lifetime in blood is a general obstacle to the application of phosphodiester DNA as a radiopharmaceutical, and a particular problem with DNA aptamer radiotracers. Serum nuclease, and also organ extraction have been proposed as the fundamental causes of this problem. 3'-biotin-streptavidin bioconjugates of the aptamers retain affinity and show extended lifetimes in blood.

The biodistribution studies confirmed that unprotected phosphodiester DNA aptamers are short-lived like other ODNs, whether in circulation or extracted blood. The biodistributions likely reflect the uptake of intact aptamers at early times. Aptamers showed rather long in vitro lifetimes by PAGE assay in fresh blood. Estimates were 5, 10, 40, 80 or >160 min, depending on the analog (ODN 1b,c,d or 2b,c,d) and animal species. These lifetime estimates imply that many analogs might be intact in vivo at 1, 5, 10 or 15 min following injection in vivo. Literature lifetimes for ODN 1a in serum (in vitro) range from 15 to 30 min. The guanine quartet structure may stabilize both ODNs 1 and 2 in serum relative to ODNs lacking secondary structure. Binding to prothrombin is an additional factor believed to extend the in vitro lifetime of ODN 1 analogs (11,18,27). Extended DNA levels in circulating blood with streptavidin aptamer bioconjugates also support this idea. Sequence dependent biodistribution differences between ODN 1 and 2 analogs also suggest uptake of intact DNA. The times of maximal organ uptake (especially liver, muscle, and kidneys) appear to be determined by the early phase DNA availability; certain organ maxima may occur at later times with the bioconjugates because the DNA availability is prolonged.

Total radioiodine (ODN plus metabolites) cleared from circulating blood in two stages in both mouse and rabbit. Labeled DNA aptamer predominated during the early stage. During the late stage, metabolites predominated (i.e. IVDU, IVU, and iodide). For unmodified aptamers ODNs 1b and 2b, the half-life in circulation is considered to be 1.0 to 1.5 min (11,18,24,27). This lifetime was scarcely increased in the 3'-biotinylated analogs, even though they were stable to nuclease in non-circulating blood. Prolonged mean lifetime in blood of 18.6 min or longer was obtained with the 3'-streptavidin bioconjugates.

It has been proposed that ODN 1a is cleared by organ extraction, especially lung extraction (11,18,27). Stabilization of aptamers by streptavidin (and not by biotin alone) suggests that ODNs might pass through a filter (analogous to the kidney glomerulus) into another compartment during natural clearance and degradation. High concentrations of ODNs 1d and 2d are found in mouse lungs (but not rabbit lungs). The above results suggest at early times the kidneys carry only 8 to 15% of the injected dose, with little in the bladder. The data indicate that the majority of ODN (85 to 92%) is extracted by organs other than the kidney; extraction models are unavailable. The multicomponent nature of the clearance kinetics suggests that more than one form of the streptavidin complex may be involved. From a biochemical standpoint, serum 3'-exonuclease is well known; 3'-end-capping of ODN is sufficient to extend the lifetime in serum (1,28). However 3'-end-capped phosphodiester ODNs are short-lived in circulating blood, suggesting that the stability problem has more components. In one example, an ODN methylphosphonate with a single 5'-phosphodiester proved stable in non-circulating blood, but truncated ODNs were recovered in circulating blood, or with organ extracts (4,9). This suggested passage of ODN back and forth between blood and solid organs. Phosphorothioate ODNs are primarily resistant to serum nuclease. They exhibit non-specific binding to serum proteins as a secondary characteristic (8). Reversing this scenario, we have bound phosphodiester ODNs to a simulated serum protein, and clearance of the ODNs was impeded.

Example 2

Di-biotinylated Aptamers

Materials and Methods

Oligodeoxynucleotides: 5'-Biotinylation was carried out with a modification of the stannyl oligonucleotide reactions (14). The 5'-Fmoc stannyl ODN on the solid support was treated with 1,8-diazabicyclo[5.4.0]undec-7-ene (DBU) (0.1M in acetonitrile, 2.5 min) to remove the Fmoc. The solid support was washed with acetonitrile, and then reacted with biotin TEG phosphoramidite (Glen Research P/N: 10–1955) according to the manufacturer's directions. The product was oxidized using 3-chloroperoxybenzoic acid, as described previously (14). The standard stannyl cleavage and deprotection procedures were carried out (14), leading to the di-biotinylated, stannyl ODN with the 5'-DMT still in place. The product ODN was purified by standard HPLC (14) using a gradient of acetonitrile in TEA bicarbonate (0.15M, pH 7.0) where a single peak was collected (tR=41 min), and divided into portions of 100 µg. The ODN was radioiodinated using $^{123}$I and a standard Iodobead procedure (14). The radioiodinated product (DMT-on) was resolved by standard HPLC at tR=35 min; this peak was collected and evaporated to dryness in the vacuum centrifuge. Detritylation was performed by suspending the dry product in aqueous acetic acid (80%, 50 µL) for 20 min at ambient temperature. The acetic acid was removed under vacuum, and the ODN was evaporated a second time in the presence of TEA (10 µL). The radioiodionated product was purified directly with a NAP-5 column. The product gave a single $^{123}$I peak (tR=19 min) on HPLC.

Aptamer stability in blood was assessed by $^{123}$I content in blood DNA in the same manner as in Example 1.

Results

Aptamer stability in blood was enhanced further (compared to 3'-biotinylated aptamer) when a doubly biotinylated aptamer (i.e. at both 3'- and 5'-ends) was conjugated with streptavidin. This would lead to a type of cyclic oligonucleotide bioconjugate with a single streptavidin tetramer, or else a linking of two streptavidin tetramers. With the di-biotin streptavidin bioconjugate a half life of roughly 90 min was found in rabbit blood.

Example 3

In situ Binding of Aptamer to Fibrinogen Clots

Reaction mixtures were made of TSTW (50 µl) supplemented with fibrinogen (0 to 10 µM), CaCl$_2$ (2 mM), [$^{125}$I]ODN (0.1 µCi, 20 nM) and IIa (0.2 to 500 nM). Atroxin replaced fibrinogen in control reactions. Following clotting, (1 hr), reaction mixtures were centrifuged. Free and bound aptamer were then determined. Results are shown in FIGS. 8A and 8B.

References

The following articles of the periodical and patent literature are cited throughout the specification. Each article is hereby incorporated by reference in its entirety by such reference.

1. Agrawal S. and Goodchild J. (1987) Oligonucleoside methylphosphonates: synthesis and enzymic degradation. Tetrahedron Lett. 28, 3539–3542.
2. Beigelman L., McSwiggen J. A., Draper K. G., et al. (1995) Chemical modification of hammerhead ribozymes. J. Biol. Chem. 270, 25702–25708.
3. Boado R. J. and Pardridge W. M. (1992) Complete protection of antisense oligonucleotides against serum nuclease degradation by an avidin-biotin system. Bioconj. Chem. 3, 519–523.
4. Boado, R. J., Kang, Y-S., Wu, D. and Pardridge, W. M. (1995) Rapid plasma clearance and metabolism in vivo of a phosphorothioate oligodeoxynucleotide with a single, internal phosphodiester bond. Drug Metab. Dispos. 23, 1297–1300.
5. Bock L. C., Griffin L. C., Latham J. A., Vermaas E. H. and Toole J. J. (1992) Selection of single-stranded DNA molecules that bind and inhibit human thrombin. Nature 355, 564–566.
6. Bock, P. E. (1992) Active-site-selective labelling of blood coagulation proteinases with fluorescence probes by the use of thioester peptide chloromethyl ketones. J. Biol. Chem. 267, 14974–14981.
7. Boskovic, D. S., Giles, A. R., and Nesheim, M. E. (1990) Studies of the role of Factor Va in the Factor Xa-catalyzed activation of Prothrombin, Fragment 1.2-Prethrombin, and dansyl-L-glutamyl-glycyl-L-arginine-Meiothrombin in the absence of phospholipid. J. Biol. Chem. 265, 10497–10505.
8. Brown D. A., Kang S. H., Gryaznov S. M. et al. (1994) Effect of phosphorothioate modification of oligodeoxynucleotides on specific protein binding. J. Biol. Chem. 269, 26801–26805.
9. Chen T. L., Miller P. S., Ts'o P.O.P., and Colvin O. M. (1990) Disposition and metabolism of oligodeoxynucleoside methylphosphonate following a single iv injection in mice. Drug Metab. Dispos. 18, 815–818.
10. Crooke S. T. (1998) Cellular uptake, distribution, and metabolism of phosphorothioate, phosphodiester and methylphosphonate oligonucleotides. In: Antisense Research and Applications (Edited by Agrawal S. and Crooke S. T.). Springer, N.Y.
11. De Anda S., Coutre S. E., Moon M. R. et al. (1994) Pilot study of the efficacy of a thrombin inhibitor for use during pulmonary bypass. Ann. Thorac. Surg. 58, 344–350.
12. Desgranges C., Razaka G., Rabaud M., Bricaud H., Balzarini J. and De Clercq E. (1983) Phosphorolysis of E-5-(2-bromovinyl)-2'-deoxyuridine (BVDU) and other 5-substituted-2'-deoxyuridines by purified human thymidine phosphorylase and intact blood platelets. Biochem. Pharmacol. 32, 3583–3590.
13. Dougan H., Rennie B. A., Lyster D. M. and Sacks S. L. (1994) No-carrier-added [123I]1-(a-D-arabinofuranosyl)-5(E)-(2-iodovinyl)uracil (IVaraU): High yielding radiolabeling via organotin and exchange reactions. Int. J. Appl. Radiat. Isot. 45, 795–801.
14. Dougan H., Hobbs J. B., Weitz J. I. and Lyster D. M. (1997) Synthesis and radioiodination of a stannyl oligoribodeoxynucleotide. Nuc. Acids Res. 25, 2897–2901.
15. Fisher J., Johnston A. M., Holland T. K., McCallum J., Pescador R., Montovani M., and Prino G. (1993)

Pharmacokinetics, absorption, distribution and disposition of [125I] defibrotide following intravenous or oral administration in the rat. Thromb. Res. 70, 77–99.
16. Gold L., Polisky B., Uhlenbeck O. and Yarus M. (1995) Diversity of oligonucleotide functions. Ann. Rev. Biochem. 64, 763–797.
17. Kubik M. F., Bell C., Fitzwater T., Watson S. R. and Tasset D. M. (1997) Isolation and characterization of 2'-fluoro, 2'-amino, and 2'-fluoro/amino modified RNA ligands to human IFN-gamma that inhibit receptor binding. J. Immunol. 159, 259–267.
18. Lee W. A., Fishback J. A., Shaw J. P., Bock L. C., Griffin L. C. and Cundy K. C. (1995) A novel oligonucleotide inhibitor of thrombin. II. Pharmacokinetics in the cynomolgus monkey. Pharm. Res. 12, 1943–1947.
19. Lin Y., Gill S. G. and Jayasena, S. D. (1994) Modified RNA sequence pools for in vitro selection. Nuc. Acids Res. 22, 5229–5234.
20. Maniatis T, Fritsch E. F. and Sambrook J. (1982) Molecular Cloning. Cold Spring Harbor Laboratory, New York. 473.
21. Manning P. J., Ringler D. H., and Newcomer C. E. (1994) Biology of the Laboratory Rabbit. Academic Press, San Diego.
22. Pieken W. A., Olsen D. B., Benseler F., Aurup H. and Eckstein F. (1991) Kinetic characterization of ribonuclease resistant 2'-modified hammerhead ribozymes. Science 253, 314–317.
23. Prince H. (1982) Blood volume in the pregnant rabbit. J. Exper. Physiol. 67, 87–95.
24. Reyderman L. and Stavachansky, S. (1998) Pharmacokinetics and biodistribution of a nucleotide-based thrombin inhibitor in rats. Pharm. Res. 15, 904–910.
25. Rosebrough S. F. (1993) Pharmacokinetics and biodistribution of radiolabeled avidin, streptavidin and biotin. Nucl. Med. Biol. 20, 663–668.
26. Samuel J., Gill M. J., Iwashina T., Tovell D. R., Tyrrell D. L., Knaus E. E. and Wiebe L. I. (1986) Pharmacokinetics and metabolism of E-5-(2-[131I]iodovinyl)-2'-deoxyuridine in dogs. Antimicrob. Agents Chemother. 29, 320–324.
27. Shaw J. P., Fishback J. A., Cundy K. C. and Lee W. A. (1995) A novel oligonucleotide inhibitor of thrombin. I. Metabolic stability in plasma and serum. Pharm. Res. 12, 1937–1942.
28. Stein C. A., Subasighe C., Shinozuka K. and Cohen J. S. (1988) Physicochemical properties of phosphorothioate oligodeoxynucleotides. Nuc. Acids Res. 16, 3209–3221.
29. Tasset D. M., Kubik M. F. and Steiner W. (1997) Oligonucleotide inhibitors of human thrombin that bind distinct epitopes. J. Mol. Biol. 272, 688–698.
30. Uphoff K. W., Bell S. D. and Ellington A. D. (1996) In vitro selection of aptamers: the dearth of pure reason. Curr. Opin. Struct. Biol. 6, 281–288.
31. Sato T, et al. (1990) Expression of a cloned streptavidin gene in Eschericia coli. Proc. Natl. Acad. Sci. 87, 1442–146.
32. Wilbur D. S. et al. (1998) Streptavidin in antibody pretargeting. Comparison of a recombinant streptavidin with two strepatvidin mutant proteins and two commercially available streptavidin proteins. Bioconjugate Chem. 9, 100–107.
33. A. Y. T. Lin et al. Complement factor C3b: Nucleic acid aptamers for complement protein C3b. WO 97/42317.
34. Y. Lin et al. (1996) High affinity specific recognition of human thyroid stimulating protein (hTSH) by in vitro selected 2'-amino-modified RNA. Nucl. Acids Res. 24, 3407–3414.
35. L. Gold et al. (1998) High affinity oligonucleotide ligands to chorionic gonadotropin hormone and related glycoprotein hormones. U.S. Pat. No. 5,837,456.

TABLES

TABLE 1: Oligodeoxynucleotide aptamers directed to human thrombin exosites 1(SEQ ID NO:1) and 2(SED ID NO:2) used in this work: a: X=Y=nil; b: X=IVDU, Y=nil; c: X=IVDU, Y=biotin; d: X=IVDU, Y=biotin-streptavidin; e: X=nil, Y=biotin; f: X=nil, Y=biotin-streptavidin.

TABLE 2: Fluorometric assay of the binding $K_d$ of bioconjugate aptamers to human α-thrombin with a fluorescein-PPACK-labeled active site. The emitted intensity (522 nm) was recorded before and after the addition of aptamer to a thrombin solution (100 nM). The incident wavelength was 492 nm.

TABLES 3A–F: Mice received [$^{125}$I] ODN (1 μCi) by tail vein, and were sacrificed and dissected at the given times. $^{125}$I was assayed in the tissues and organs. Except where indicated, n=3. The identity of the ODN is indicated on each chart.

TABLES 4A–F: Anaesthetized female New Zealand rabbits received [$^{123}$I] ODN (0.5 mCi) by ear vein. Rabbits were laid in the supine position on the detector and images were obtained based on ten second counting frames. The biodistribution was estimated from analysis of counts in the region of interest compared to the total counts.

TABLE 5: Blood metabolites were analyzed by HPLC following the injection of [$^{123}$I]ODN 1b into a female New Zealand rabbit. Plasma was obtained from blood samples (0.5 mL), and was treated with an equal volume of methanol at 0° C. The supernatant was evaporated, resuspended, and filtered, prior to HPLC (12,26). Reverse phase HPLC employed a gradient of methanol (27% to 62% over 18 min) in aqueous $KH_2PO_4$ (0.01 M, 2 ml/min). IVDU and IVU were identified by migration with standards. Samples (1 mL) were collected in plastic vials for quantitative measurement in a well-type counter.

TABLE 6: [$^{125}$I] ODN was incubated in 40 æL blood freshly drawn from a mouse for times indicated at 36° C. Plasma (2.5 μL) was diluted in formamide (10 μL) or else urea (10 μL; urea (7 M), glycerol (10%)) and the DNA was resolved by PAGE. The autoradiograph was scored for the presence (+) or absence (−) of full length aptamer.

TABLE 7: [$^{125}$I] ODN was incubated in 40 μL blood freshly drawn from a rabbit for times indicated at 39° C. The procedure was otherwise similar to Table 6.

TABLE 1

| Oligodeoxynucleotide Aptamers Directed to Human Thrombin Exosites 1 and 2[1] |
|---|
| ODN 1a–e  5'->:-d(GGTTGGTGTGGTTGG)-Y-3' (exosite 1) |
| ODN 2a–e  5'->:-d(AGTCCGTGGTAGGGCAGGTTGGGGTGACT)-Y-3' (exosite 2) | a: X = Y nil:
b: X = IVDU, Y = nil;
c: X = IVDU, Y = biotin;
d: X = IVDU, Y = biotin-streptavidin;
e: X = nil, Y = biotin;
f: X = nil, Y = biotin-streptavidin.

TABLE 3

Results of Biodistributions Studies in Mice

| Time (min) | Blood | Liver | Kidneys | Spleen | Stomach | Lung | Heart | Muscle | Brain |
|---|---|---|---|---|---|---|---|---|---|
| A. ODN 1b | | | | | | | | | |
| 0.5 | 5.80 ± 31.80 | 7.58 ± 5.35 | 3.41 ± 2.42 | 0.07 ± 0.53 | 0.35 ± 0.25 | 1.65 ± 1.17 | 0.54 ± 0.39 | 13.12 ± 8.89 | 0.27 ± 0.19 |
| 1.0 | 5.18 ± 0.89 | 20.00 ± 1.09 | 6.75 ± 0.84 | 0.26 ± 0.84 | 0.50 ± 0.02 | 2.42 ± 0.35 | 0.69 ± 0.10 | 20.24 ± 0.79 | 0.31 ± 0.04 |
| 1.5 | 6.86 ± 0.87 | 25.10 ± 0.89 | 9.33 ± 0.83 | 0.25 ± 0.04 | 0.51 ± 0.03 | 1.56 ± 0.40 | 0.73 ± 0.04 | 19.98 ± 0.76 | 0.22 ± 0.01 |
| 2.0 | 2.28 ± 1.20 | 23.51 ± 1.74 | 8.31 ± 0.28 | 0.27 ± 0.02 | 0.50 ± 0.02 | 1.54 ± 0.19 | 0.74 ± 0.11 | 21.77 ± 0.75 | 0.16 ± 0.02 |
| 2.5 | 8.79 ± 1.38 | 22.46 ± 0.84 | 6.88 ± 0.39 | 0.26 ± 0.04 | 0.46 ± 0.01 | 0.99 ± 0.08 | 0.68 ± 0.02 | 21.00 ± 0.64 | 0.14 ± 0.01 |
| 5.0 | 4.48 ± 0.72 | 17.46 ± 0.51 | 5.83 ± 0.49 | 0.21 ± 0.01 | 0.43 ± 0.04 | 1.05 ± 0.24 | 0.56 ± 0.03 | 22.02 ± 1.50 | 0.14 ± 0.03 |
| 10.0 | 1.26 ± 0.61 | 10.01 ± 0.15 | 3.02 ± 0.14 | 0.20 ± 0.01 | 0.46 ± 0.07 | 0.65 ± 0.05 | 0.43 ± 0.02 | 20.15 ± 1.06 | 0.14 ± 0.02 |
| 15.0 | 0.26 ± 0.15 | 8.24 ± 0.43 | 3.11 ± 0.34 | 0.21 ± 0.03 | 0.62 ± 0.13 | 0.55 ± 0.03 | 0.40 ± 0.04 | 20.56 ± 0.60 | 0.24 ± 0.01 |
| B. ODN 1c | | | | | | | | | |
| 0.5 | 5.78 ± 10.51 | 9.55 ± 2.15 | 4.88 ± 0.84 | 0.13 ± 0.03 | 0.38 ± 0.05 | 5.31 ± 0.94 | 0.83 ± 0.05 | 13.48 ± 0.45 | 0.59 ± 0.03 |
| 1.0 | 2.94 ± 5.32 | 15.32 ± 1.41 | 5.90 ± 0.96 | 0.24 ± 0.03 | 0.47 ± 0.04 | 4.37 ± 0.27 | 0.77 ± 0.07 | 15.75 ± 1.38 | 0.43 ± 0.04 |
| 1.5 | 5.93 ± 3.70 | 20.23 ± 0.73 | 7.79 ± 0.28 | 0.33 ± 0.05 | 0.58 ± 0.03 | 4.95 ± 1.74 | 0.76 ± 0.04 | 16.91 ± 0.99 | 0.33 ± 0.01 |
| 2.0 | 5.03 ± 2.54 | 21.15 ± 0.55 | 9.70 ± 1.42 | 0.37 ± 0.05 | 0.64 ± 0.15 | 2.72 ± 0.74 | 0.67 ± 0.04 | 17.71 ± 2.50 | 0.26 ± 0.04 |
| 2.5 | 6.49 ± 5.83 | 19.13 ± 2.66 | 8.93 ± 1.32 | 0.35 ± 0.05 | 0.55 ± 0.02 | 2.45 ± 0.44 | 0.61 ± 0.08 | 20.65 ± 1.51 | 0.24 ± 0.01 |
| 5.0 | 8.71 ± 1.05 | 15.60 ± 1.00 | 7.76 ± 0.94 | 0.29 ± 0.03 | 0.49 ± 0.05 | 1.36 ± 0.16 | 0.59 ± 0.02 | 27.42 ± 1.13 | 0.16 ± 0.02 |
| 10.0 | 4.04 ± 0.72 | 12.00 ± 0.39 | 7.53 ± 0.60 | 0.24 ± 0.02 | 0.57 ± 0.06 | 1.13 ± 0.44 | 0.44 ± 0.02 | 25.91 ± 2.87 | 0.16 ± 0.01 |
| 15.0 | 9.17 ± 0.69 | 7.59 ± 0.35 | 3.75 ± 0.69 | 0.23 ± 0.01 | 0.70 ± 0.09 | 0.52 ± 0.09 | 0.31 ± 0.04 | 17.86 ± 2.02 | 0.17 ± 0.05 |
| C. ODN 1d | | | | | | | | | |
| 0.5 | 15.20 ± 4.90 | 8.92 ± 0.36 | 2.10 ± 0.17 | 0.16 ± 0.04 | 0.18 ± 0.01 | 4.12 ± 1.27 | 0.49 ± 0.02 | 7.48 ± 0.40 | 0.37 ± 0.03 |
| 1.0 | 15.72 ± 0.37 | 11.25 ± 1.66 | 2.83 ± 0.36 | 0.35 ± 0.06 | 0.25 ± 0.06 | 4.69 ± 1.89 | 0.5 ± 0.03 | 8.99 ± 1.47 | 0.41 ± 0.06 |
| 1.5 | 12.81 ± 1.30 | 11.81 ± 2.21 | 3.42 ± 1.21 | 0.38 ± 0.05 | 0.24 ± 0.10 | 4.66 ± 1.22 | 0.55 ± 0.06 | 9.78 ± 2.16 | 0.33 ± 0.02 |
| 2.0 | 55.55 ± 8.34 | 10.95 ± 2.27 | 2.97 ± 0.86 | 0.46 ± 0.09 | 0.23 ± 0.13 | 4.02 ± 2.32 | 0.64 ± 0.13 | 10.25 ± 3.19 | 0.41 ± 0.03 |
| 2.5 | 52.86 ± 5.86 | 13.02 ± 2.60 | 3.60 ± 0.64 | 0.38 ± 0.06 | 0.21 ± 0.04 | 6.50 ± 0.27 | 0.59 ± 0.13 | 9.15 ± 0.92 | 0.36 ± 0.05 |
| 5.0 | 54.97 ± 2.86 | 13.49 ± 2.21 | 3.39 ± 0.60 | 0.58 ± 0.19 | 0.24 ± 0.04 | 4.91 ± 1.75 | 0.58 ± 0.03 | 11.98 ± 1.16 | 0.32 ± 0.04 |
| 10.0 | 47.43 ± 2.28 | 12.68 ± 0.76 | 3.24 ± 0.20 | 0.43 ± 0.08 | 0.26 ± 0.02 | 4.60 ± 0.56 | 0.47 ± 0.05 | 13.51 ± 0.07 | 0.31 ± 0.01 |
| 15.0 | 39.18 ± 2.74 | 11.94 ± 0.30 | 3.06 ± 0.41 | 0.47 ± 0.04 | 0.32 ± 0.01 | 3.55 ± 1.20 | 0.56 ± 0.02 | 16.65 ± 2.09 | 0.29 ± 0.02 |
| D. ODN 2b | | | | | | | | | |
| 0.5 | 40.99 ± 5.41 | 16.78 ± 0.73 | 7.63 ± 1.06 | 0.36 ± 0.08 | 0.73 ± 0.05 | 3.90 ± 1.45 | 0.65 ± 0.06 | 16.4 ± 1.39 | 0.30 ± 0.03 |
| 1.0 | 33.29 ± 7.51 | 19.4 ± 0.81 | 10.1 ± 0.95 | 0.41 ± 0.02 | 0.68 ± 0.06 | 2.91 ± 0.66 | 0.67 ± 0.01 | 19.87 ± 0.78 | 0.21 ± 0.01 |
| 1.5 | 30.90 ± 1.91 | 15.98 ± 0.3 | 12.4 ± 0.60 | 0.45 ± 0.02 | 0.51 ± 0.01 | 2.64 ± 0.28 | 0.60 ± 0.08 | 18.27 ± 1.41 | 0.18 ± 0.04 |
| 2.0 | 20.49 ± 2.39 | 12.92 ± 2.65 | 8.14 ± 1.52 | 0.36 ± 0.05 | 0.62 ± 0.08 | 1.84 ± 0.20 | 0.57 ± 0.09 | 21.29 ± 2.76 | 0.16 ± 0.01 |
| 2.5 | 18.12 ± 1.83 | 12.89 ± 1.12 | 8.02 ± 2.55 | 0.47 ± 0.02 | 0.66 ± 0.05 | 1.89 ± 0.60 | 0.60 ± 0.06 | 20.96 ± 1.2 | 0.18 ± 0.02 |
| 5.0 | 13.39 ± 1.40 | 9.29 ± 0.53 | 4.45 ± 1.63 | 0.35 ± 0.07 | 0.60 ± 0.12 | 1.05 ± 0.24 | 0.44 ± 0.04 | 21.14 ± 4.69 | 0.16 ± 0.01 |
| 10.0 | 8.22 ± 2.77 | 5.18 ± 2.19 | 2.18 ± 0.74 | 0.26 ± 0.13 | 0.46 ± 0.23 | 1.01 ± 0.13 | 0.28 ± 0.11 | 13.83 ± 6.41 | 0.11 ± 0.05 |
| 15.0 | 10.63 ± 0.81 | 6.2 ± 0.33 | 2.53 ± 0.19 | 0.33 ± 0.03 | 0.78 ± 0.06 | 0.92 ± 0.16 | 0.36 ± 0.03 | 17.53 ± 0.44 | 0.17 ± 0.02 |
| E. ODN 2c | | | | | | | | | |
| 0.5 | 78.48 ± 7.29 | 11.84 ± 3.08 | 5.91 ± 1.38 | 0.1 ± 0.11 | 0.40 ± 0.15 | 3.74 ± 0.98 | 1.02 ± 0.17 | 13.68 ± 0.90 | 0.43 ± 0.06 |
| 1.0 | 53.40 ± 2.80 | 14.95 ± 0.15 | 11 ± 0.12 | 0.32 ± 0.02 | 0.52 ± 0.01 | 3.81 ± 2.04 | 0.69 ± 0.08 | 13.74 ± 1.78 | 0.28 ± 0.02 |
| 1.5 | 36.27 ± 3.25 | 19.16 ± 0.75 | 13.8 ± 0.93 | 0.54 ± 0.19 | 0.45 ± 0.09 | 2.22 ± 0.92 | 0.68 ± 0.08 | 15.23 ± 1.77 | 0.21 ± 0.04 |
| 2.0 | 25.10 ± 2.75 | 17.5 ± 1.32 | 12.6 ± 0.68 | 0.68 ± 0.07 | 0.80 ± 0.10 | 1.61 ± 0.14 | 0.51 ± 0.06 | 16.18 ± 1.67 | 0.21 ± 0.01 |
| 2.5 | 18.47 ± 11.81 | 13.85 ± 9.72 | 11.3 ± 7.87 | 0.48 ± 0.34 | 0.67 ± 0.47 | 1.47 ± 0.90 | 0.37 ± 0.24 | 13.78 ± 9.28 | 0.10 ± 0.06 |
| 5.0 | 15.12 ± 0.19 | 13.14 ± 0.93 | 9.34 ± 2.47 | 0.51 ± 0.03 | 0.66 ± 0.04 | 1.52 ± 0.04 | 0.42 ± 0.05 | 20.10 ± 2.02 | 0.17 ± 0.02 |
| 10.0 | 11.66 ± 0.03 | 8.31 ± 0.15 | 4.42 ± 0.15 | 0.37 ± 0.03 | 0.68 ± 0.04 | 1.19 ± 0.07 | 0.31 ± 0.01 | 18.86 ± 0.23 | 0.12 ± 0.01 |
| 15.0 | 8.15 ± 3.54 | 5.83 ± 2.46 | 3.04 ± 1.3 | 0.22 ± 0.16 | 0.97 ± 0.32 | 0.83 ± 0.38 | 0.27 ± 0.10 | 13.02 ± 7.51 | 0.10 ± 0.05 |
| F. ODN 2d | | | | | | | | | |
| 0.5 | 84.40 ± 4.85 | 14.58 ± 2.10 | 3.05 ± 0.31 | 0.12 ± 0.01 | 0.22 ± 0.04 | 3.57 ± 1.54 | 1.00 ± 0.03 | 8.50 ± 0.48 | 0.41 ± 0.07 |
| 1.0 | 78.11 ± 0.78 | 17.12 ± 0.94 | 3.61 ± 0.29 | 0.32 ± 0.04 | 0.24 ± 0.02 | 3.77 ± 0.46 | 0.84 ± 0.12 | 8.70 ± 1.58 | 0.4 ± 0.02 |
| 1.5 | 63.25 ± 6.57 | 18.12 ± 2.13 | 3.84 ± 0.68 | 0.42 ± 0.08 | 0.27 ± 0.07 | 3.01 ± 0.48 | 0.84 ± 0.07 | 9.04 ± 1.56 | 0.38 ± 0.07 |
| 2.0 | 58.50 ± 0.88 | 17.23 ± 2.35 | 4.12 ± 0.46 | 0.42 ± 0.03 | 0.37 ± 0.06 | 3.00 ± 0.62 | 0.88 ± 0.04 | 11.30 ± 0.66 | 0.32 ± 0.1 |
| 2.5 | 46.24 ± 6.42 | 19.69 ± 6.62 | 4.68 ± 0.94 | 0.45 ± 0.06 | 0.43 ± 0.19 | 2.05 ± 0.64 | 0.71 ± 0.06 | 9.47 ± 1.83 | 0.11 ± 0.05 |
| 5.0 | 41.48 ± 3.53 | 23.84 ± 0.46 | 5.11 ± 0.37 | 0.57 ± 0.07 | 0.35 ± 0.03 | 2.52 ± 0.26 | 0.66 ± 0.02 | 16.31 ± 0.33 | 0.23 ± 0.01 |
| 10.0 | 27.18 ± 1.87 | 19.56 ± 1.82 | 4.13 ± 0.71 | 0.56 ± 0.10 | 0.45 ± 0.02 | 1.71 ± 0.42 | 0.56 ± 0.04 | 19.40 ± 0.54 | 0.23 ± 0.01 |
| 15.0 | 22.37 ± 2.10 | 13.92 ± 0.87 | 3.43 ± 0.19 | 0.48 ± 0.04 | 0.65 ± 0.29 | 1.64 ± 0.47 | 0.52 ± 0.02 | 18.69 ± 0.55 | 0.19 ± 0.01 |

Mice recd red: $^{128}$U oligodeoxynucleotide, ODN) (1 μG) by call vein and were sacrificed and dissected at given times. $^{181}$I was assayed in the tissues and organ to give % injected dose per organ. Except where indicated, N = 3. The identity of the ODN is indicated on each chart.

TABLE 4

Results of Biodistribution Studies in Rabbits

| Time (min) | Liver | Kidney | Bladder | Lung | Heart | Remaining body |
|---|---|---|---|---|---|---|
| ODN 1b | | | | | | |
| 0.5 | 27.10 | 9.12 | 3.91 | 3.47 | 10.60 | 45.80 |
| 1.0 | 28.40 | 10.48 | 3.94 | 3.27 | 7.46 | 46.45 |
| 0.5 | 16.50 | 10.58 | 7.13 | 3.21 | 5.68 | 56.90 |
| 10.0 | 16.50 | 7.24 | 15.30 | 3.38 | 5.16 | 52.42 |
| 20.0 | 12.30 | 6.22 | 19.40 | 3.22 | 4.61 | 54.23 |
| 30.0 | 10.70 | 6.12 | 20.20 | 3.17 | 4.39 | 55.42 |
| ODN 1c | | | | | | |
| 0.50 | 18.10 | 10.20 | 1.10 | 4.20 | 4.20 | 62.20 |
| 1.00 | 18.20 | 14.60 | 1.10 | 3.70 | 3.60 | 58.80 |
| 5.00 | 12.20 | 14.60 | 1.40 | 1.90 | 1.80 | 68.10 |
| 10.00 | 9.90 | 12.40 | 4.90 | 1.70 | 1.50 | 69.60 |
| 20.00 | 8.10 | 9.60 | 8.20 | 1.50 | 1.30 | 71.30 |
| ODN 1d | | | | | | |
| 0.5 | 22.90 | 4.80 | 1.80 | 4.40 | 7.50 | 55.50 |
| 1.0 | 23.10 | 5.00 | 2.10 | 4.60 | 7.40 | 57.74 |
| 5.0 | 17.90 | 6.20 | 2.50 | 2.10 | 3.10 | 65.62 |
| 10.0 | 15.90 | 6.20 | 4.90 | 1.70 | 2.40 | 66.14 |
| 20.0 | 12.50 | 5.60 | 9.40 | 1.40 | 1.90 | 66.49 |
| 30.0 | 10.40 | 5.40 | 12.20 | 1.20 | 1.60 | 66.41 |
| ODN 2b | | | | | | |
| 0.5 | 36.30 | 11.60 | 2.10 | 1.40 | 10.60 | 37.80 |
| 1.0 | 37.20 | 14.80 | 2.40 | 1.20 | 17.60 | 36.30 |
| 5.0 | 26.80 | 13.20 | 4.10 | 1.70 | 4.60 | 49.60 |
| 10.0 | 20.90 | 11.40 | 10.10 | 1.60 | 4.10 | 51.90 |
| 20.0 | 16.60 | 9.20 | 15.20 | 1.50 | 3.60 | 53.70 |
| 30.0 | 14.30 | 8.20 | 18.40 | 1.40 | 3.40 | 54.30 |
| ODN 2c | | | | | | |
| 0.5 | 35.10 | 11.20 | 3.20 | 1.80 | 9.10 | 39.60 |
| 1.0 | 35.90 | 13.20 | 3.50 | 1.40 | 7.90 | 38.10 |
| 5.0 | 23.80 | 12.20 | 4.20 | 1.50 | 3.80 | 54.50 |
| 10.0 | 19.70 | 10.40 | 9.10 | 1.40 | 3.30 | 56.10 |
| 20.0 | 15.70 | 7.40 | 14.80 | 1.20 | 2.80 | 58.10 |
| 30.0 | 13.90 | 6.40 | 17.80 | 1.20 | 2.60 | 58.10 |
| ODN 2d | | | | | | |
| 0.5 | 25.30 | 8.40 | 3.30 | 3.20 | 10.30 | 49.50 |
| 1.0 | 32.70 | 8.40 | 3.00 | 2.80 | 8.10 | 45.00 |
| 5.0 | 32.70 | 9.60 | 3.50 | 2.20 | 4.40 | 47.60 |
| 10.0 | 27.80 | 9.20 | 5.90 | 2.10 | 3.80 | 51.20 |
| 20.0 | 19.60 | 8.80 | 10.40 | 1.80 | 3.20 | 56.20 |
| 30.0 | 15.60 | 7.80 | 17.60 | 1.70 | 2.80 | 54.50 |

Anesthetized female New Zealand rabbits received [$^{123}$I] oligodeoxynucleotide (ODN) (0.5 mCi) by ear vein. Rabbits were laid in the supine position on the detector and images were obtained based on 10 sec counting frames. The biodistribution (% injected dose per organ) was estimated from analysis of counts in the region of interest compared with the total counts.

TABLE 5

Blood Metabolites

| | 5 min | 15 min | 30 min |
|---|---|---|---|
| IVDU | 46.7% | 23.4% | 11.6% |
| IVU | 13.2% | 7.5% | 5.0% |
| Iodide | 32.8% | 63.3% | 78.3% |

Blood metabolites were analyzed by high performance liquid chromatography (HPLC) following the injection of [$^{123}$I] oligodeoxynucleotide (ODN) 1b into a female New Zealand rabbit. Plasma was obtained from blood samples (0.5 mL), and was treated with an equal volume of methanol at 0° C. The supernatant was evaporated, resuspended, and filtered, prior to HPLC (12, 26). Reverse phase HPLC employed a gradient of methanol (27–62% over 18 min) in aqueous $KH_2PO_4$ (0.01 M, 2 mL/min). 5-(2-iodovinyl)-2'-deoxyiodine (IVDU) and [$^{123}$I]5-(2-iodovinyl)uracil (IIVU) were identified by migration with standards. Samples (1 mL) were collected in plastic vials for quantitative measurement in a well-type counter.

TABLE 6

Results of Autoradiography of Mouse Blood

| ODN | 5 min | 10 min | 20 min | 40 min | 80 min | 160 min |
|---|---|---|---|---|---|---|
| ODN-1b | + | + | (+) | − | − | − |
| ODN-1c | + | + | + | + | + | − |
| ODN-1d | + | + | + | + | + | − |
| ODN-2b | + | + | (+) | − | − | − |
| ODN-2c | + | + | + | + | + | − |
| ODN-2d | + | + | + | + | + | + |

[$^{125}$I] Oligodeoxynucleotide (ODN) was incubated in 40 æL blood freshly drawn from a mouse for times indicated at 36° C. Plasma (2.5 μL) was diluted in formamide (10 μL) or urea (10 μL; urea (7M), glycerol (10%)) and the DNA was resolved by polyvinylamide gel electrophoresis. The autoradiograph was scored for the presence (+) or absence (−) of full length aptamer.

TABLE 7

Results of Autoradiography of Rabbit Blood

| ODN | 5 min | 10 min | 20 min | 40 min | 80 min | 160 min |
|---|---|---|---|---|---|---|
| ODN-1b | + | (−) | − | − | − | − |
| ODN-1c | + | + | + | + | + | − |
| ODN-1d | − | + | + | + | − | − |
| ODN-2b | − | (−) | − | − | − | − |
| ODN-2c | − | + | + | + | (+) | − |
| ODN-2d | − | + | + | + | + | + |

[$^{125}$I] Oligodeoxynucleotide (ODN) was incubated in 40 μL blood freshly drawn from a rabbit for times indicated at 39° C. The procedure was otherwise similar to Table 6.

TABLE 2

Affinity ($k_D$) of Bioconjugate Aptamers

| ODN | Type | $k_D$ |
|---|---|---|
| ODN 1a | Unmodified | 45 nM |
| ODN 1e | 3'-Biotin | 55 nM |
| ODN 1f | 3'-Streptavidin | 41 nM, 99 nM |
| ODN 2a | Unmodified | 16.5 nM |
| ODN 2e | 3'-Biotin | 85 nM |
| ODN 2f | 3'-Streptavidin | 89 nM, 110 nM |

Fluorometric assay of the binding $k_D$ of bioconjugate aptamers to human α-thrombin with a fluorescein-PPACK-labeled active site. The emitted intensity (522 nm) was recorded before and after the addition of aptamer to a thrombin solution (100 nM). The incident wavelength was 492 nm.

What is claimed:

1. A composition comprising:
   a nucleic acid that binds to thrombin; and
   a protein attached to said nucleic acid at either the 5' end or the 3' end or both wherein said protein is streptavidin or a variant of streptavidin that retains biotin binding activity.

2. The composition of claim 1, wherein said nucleic acid is derivatized at the 5' or 3' end or at both the 5' and 3' ends with a reagent specific for binding to said protein thereby forming a complex between said reagent and said protein.

3. The composition of claim 2, further comprising a linker that covalently attaches said protein to said nucleic acid or said reagent to said nucleic acid.

4. The composition of claim 2, wherein said reagent is biotin.

5. The composition of claim 3, wherein said reagent is biotin that is covalently attached to a linker.

6. The composition of claim any one of claims 1–5 wherein said composition is further labeled with a radioactive label.

7. The composition of claim 6, wherein said radioactive label is $^{123}$I, $^{124}$I, $^{125}$I, $^{131}$I, $^{99m}$Tc, $^{186}$Re, $^{188}$Re, $^{64}$Cu, $^{67}$Cu, $^{212}$Bi, $^{67}$Ga, $^{90}$Y, $^{111}$In, $^{18}$F, $^{3}$H, $^{14}$C, $^{35}$S or $^{32}$P.

8. A method for imaging blood clots in vivo comprising intravenously administering to a subject the composition of claim 6 and imaging the emission from said radioactive label.

9. A method for preventing coagulation of blood in a subject requiring anticoagulation treatment comprising intravenously administering an amount of the composition of claim 6 effective to inhibit coagulation to said subject.

10. A method for inhibiting degradation of a nucleic acid in the blood comprising attaching streptavidin or a variant thereof that retains biotin binding activity to said nucleic acid at the 5' or 3' end or at both the 5' and 3' ends.

11. The method of claim 10, wherein said nucleic acid is derivatized with biotin and the streptavidin or variant thereof binds to the biotin.

12. The method of claim 10 wherein said nucleic acid is DNA, 2'-fluoropyrimidine RNA or 2'-aminopyrimidine RNA.

13. A composition comprising: a nucleic acid, that is derivatized at the 5' or 3' end or at both the 5' and 3' ends with streptavidin or a variant of streptavidin that retains biotin binding activity, that specifically binds to thrombin, wherein said nucleic acid is 2'-fluoropyrimidine RNA or 2'-aminopyrimidine RNA.

14. The composition of claim 13 wherein the wherein said nucleic acid is derivatized at the 5' or 3' end or at both the 5' and 3' ends with a reagent specific for binding to said streptavidin or variant thereof thereby forming a complex between said reagent and said streptavidin or variant thereof.

15. The composition of claim 14, further comprising a linker that covalently attaches said reagent to said nucleic acid.

16. The composition of claim 15, wherein said reagent is biotin that is covalently attached to said linker.

17. The composition of claim 13, wherein said protein is covalently attached to said nucleic acid through a linker.

18. The composition of claim 13, wherein said nucleic acid is less than 50 nucleotides long.

19. The composition of claim 13, wherein said composition is further labeled with a radioactive label.

20. The composition of claim 19, wherein said radioactive label is $^{123}$I, $^{124}$I, $^{125}$I, $^{131}$I, $^{99m}$Tc, $^{186}$Re, $^{188}$Re, $^{64}$Cu, $^{67}$Cu, $^{212}$Bi, $^{213}$Bi, $^{67}$Ga, $^{90}$Y, $^{111}$In, $^{18}$F, $^{3}$H, $^{14}$C, $^{35}$S or $^{32}$P.

21. A method for imaging blood clots in vivo comprising intravenously administering to a subject the composition of claim 19 and imaging the emission from said radioactive label.

22. A method for preventing coagulation of blood in a subject requiring anticoagulation treatment comprising intravenously administering an amount of the composition of claim 13 effective to inhibit coagulation to said subject.

23. The composition of claim 1, wherein the nucleic acid comprises nucleotides having the sequence of SEQ ID NO: 1 or SEQ ID NO: 2.

24. The composition of claim 13, wherein the nucleic acid comprises nucleotides having the RNA sequence corresponding to SEQ ID NO: 1 or SEQ ID NO: 2.

25. A composition comprising:

a nucleic acid that specifically binds to thrombin; and a protein attached to said nucleic acid at either the 5' end or the 3' end or both wherein said protein is streptavidin or a variant of streptavidin that retains biotin binding activity;

wherein the nucleic acid is obtained by a selection process comprising:
- i) providing a pool of polynucleotides each comprising a randomized sequence between segments of constant sequence;
- ii) contacting the pool of polynucleotides with thrombin in a binding solution to obtain polynucleotide-:thrombin complexes and unbound polynucleotides;
- iii) separating polynucleotide:thrombin complexes from unbound polynucleotides; and
- iv) isolating the polynucleotides of the polynucleotide-:thrombin complexes.

26. The composition of claim 25, wherein the process of obtaining the nucleic acid further comprises:
- v) amplifying the polynucleotides isolated from the polynucleotide:thrombin complexes and
- vi) repeating the selection process using a binding solution during the contacting step ii) so that a higher affinity of the nucleic acid for the target protein is required to form a polynucleotide:thrombin complex.

27. The composition of claim 26, wherein in step vi) the selection process is repeated using a binding solution during the contacting step ii) having an increased salt concentration.

28. The method of claim 26, in which the amplifying step v) is performed by at least one polymerase chain reaction.

29. The method of claim 25, in which the isolating step iv) comprises cloning of the polynucleotides.

30. The composition of claim 1 or claim 13, wherein the nucleic acid component comprises a nucleotide sequence that forms a guanine quartet.

31. The composition of claim 1 or claim 13, wherein the nucleic acid component comprises residues 1–6 of SEQ ID NO. 1 linked to the 5' end of residues 10–16 of SEQ ID NO. 1 by a sequence of three nucleotides.

* * * * *